United States Patent
Ogikubo

(10) Patent No.: US 7,612,330 B2
(45) Date of Patent: Nov. 3, 2009

(54) OPTICAL SCANNING PROBE, OPTICAL SCANNING PROBE DEVICE AND METHOD FOR CONTROLLING THE OPTICAL SCANNING PROBE

(75) Inventor: Shinya Ogikubo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/204,559

(22) Filed: Sep. 4, 2008

(65) Prior Publication Data

US 2009/0057543 A1 Mar. 5, 2009

(30) Foreign Application Priority Data

Sep. 4, 2007 (JP) .............................. 2007-229023

(51) Int. Cl.
G02B 23/00 (2006.01)
G02B 26/08 (2006.01)
G02B 26/10 (2006.01)
H01J 3/14 (2006.01)
A61B 1/00 (2006.01)

(52) U.S. Cl. ................... 250/234; 250/235; 600/160; 600/170; 600/173; 600/177; 600/118; 359/210.2; 359/213.1; 359/225.1

(58) Field of Classification Search ......... 250/234–236; 359/196.1–226.3; 600/101–183
See application file for complete search history.

(56) References Cited

U.S. PATENT DOCUMENTS

| | | | |
|---|---|---|---|
| 6,037,583 A * | 3/2000 | Moehler et al. | ............. 250/235 |
| 6,433,910 B2 * | 8/2002 | Suga | ....................... 359/212.1 |
| 7,252,634 B2 * | 8/2007 | Mizumo | ..................... 600/160 |
| 7,450,244 B2 * | 11/2008 | Xie | .............. 356/479 |
| 2006/0120706 A1 * | 6/2006 | Cho et al. | ..................... 396/17 |
| 2006/0152106 A1 * | 7/2006 | Yan et al. | ..................... 310/309 |
| 2006/0167344 A1 * | 7/2006 | Mizumo | ..................... 600/168 |
| 2006/0195019 A1 * | 8/2006 | Premachandran et al. | ... 600/300 |
| 2007/0091406 A1 * | 4/2007 | Filhol et al. | ................. 359/210 |
| 2007/0167710 A1 * | 7/2007 | Unal et al. | .................. 600/407 |
| 2007/0299303 A1 * | 12/2007 | Ogikubo | ..................... 600/102 |
| 2008/0186501 A1 * | 8/2008 | Xie | ............. 356/450 |
| 2008/0304123 A1 * | 12/2008 | Wang et al. | ................. 359/196 |
| 2009/0021818 A1 * | 1/2009 | Weir et al. | ................... 359/224 |
| 2009/0057543 A1 * | 3/2009 | Ogikubo | ..................... 250/234 |

(Continued)

FOREIGN PATENT DOCUMENTS

JP 11-52278 A 2/1999

(Continued)

*Primary Examiner*—John R Lee
(74) *Attorney, Agent, or Firm*—Sughrue Mion, PLLC

(57) ABSTRACT

An optical scanning probe is provided and includes an optical scanning element which scans a subject with light, and a signal switching section for switching a drive signal for making the optical scanning element perform optical scanning. The optical scanning element includes a movable portion having a micro mirror which is displaced in a first rotating direction and a second rotating direction, and first and second drivers which apply physical acting forces to the movable portion. The signal switching section has a function for switching a driving preparation signal for attracting the movable portion in either the first rotating direction or the second rotating direction into a scanning drive signal for attracting the movable portion in the first rotating direction and the second rotating direction alternately. The maximum voltage of the driving preparation signal is set value to be higher than the maximum voltage of the scanning drive signal.

19 Claims, 20 Drawing Sheets

U.S. PATENT DOCUMENTS

2009/0080046 A1 * 3/2009 Ogikubo .................... 359/199

FOREIGN PATENT DOCUMENTS

| JP | 2000-310743 A | 11/2000 |
| JP | 2001-311900 A | 11/2001 |
| JP | 2002-267995 A | 9/2002 |
| JP | 2002-328329 A | 11/2002 |

* cited by examiner

P-P SECTION

OPTICAL SCANNING PROBE, OPTICAL SCANNING PROBE DEVICE AND METHOD FOR CONTROLLING THE OPTICAL SCANNING PROBE

This application is based on and claims priority under 35 U.S.C. §119 from Japanese Patent Application No. 2007-229023 filed Sep. 4, 2007, the entire disclosure of which is herein incorporated by reference.

BACKGROUND OF THE INVENTION

1. Field of the Invention

The present invention relates to an optical scanning probe and an optical scanning device including a micro mirror which is displaced by a physical acting force, and a method for controlling the optical scanning probe, and more specifically, to a technique to be preferably used for a diagnostic probe of a medically-applied endoscope device.

2. Description of Related Art

Recently, as means for observing the states of the surface and the inside of body tissues and cells, an optical scanning type confocal optical microscope including an optical scanning element is known, and application of similar techniques using optical scanning elements to endoscopes is also considered. Optical scanning type microscopes and endoscopes have a resolution over the resolution limitation of general optical systems, and advantages that it can form three-dimensional images.

As this optical scanning element, various optical scanning elements are proposed, and in particular, an optical scanning element in which a micro mirror manufactured by applying a micro-machining technique is constructed so as to oscillate back and forth by an electrostatic force around a twist beam as a rotation axis is considered dominantly as practicable. The optical scanning element oscillates back and forth a mirror substrate supported by two beams provided on the same straight line around the two beams serving as a twist rotation axis by an electrostatic attractive force between electrodes provided at positions opposed to the mirror substrate.

The optical scanning element formed by a micro machining technique has a simpler structure and can be formed collectively through a semiconductor process in comparison with a related-art optical scanning element using a rotatable polygon mirror, so that the optical scanning element can be easily downsized and manufactured at low cost, and it has a single reflective surface, so that it does not have low accuracy among the reflective surfaces as in the case of the polygon mirror, and a higher speed can also be realized by reciprocating scanning.

As the above-described optical scanning element, for example, elements having the structures disclosed in JP-A-2000-310743, JP-A-11-52278, JP-A-2001-311900, JP-A-2002-267995 and JP-A-2002-328329 are known.

The constructions of the optical scanning elements disclosed in JP-A-2000-310743 are shown in FIGS. 22A and 22B. These optical scanning elements 1A and 1B are constructed on the assumption that they are applied to endoscopes, and adopt general electrostatic driving as the optical scanning element driving method. In other words, as shown in FIG. 22A, a voltage is applied between movable electrodes 3a and 3b provided on the left and right of the movable portion 2 and fixed electrodes not shown and provided oppositely to the movable electrodes, and by a generated electrostatic force, the movable portion 2 is rotatively displaced around beams 4 as a central axis. In the figures, the hatched areas show mirror portions. FIG. 22A shows a construction of a uniaxial mirror, and FIG. 22B shows a construction of a biaxial mirror which is rotatively displaced around the beams 4 and beams 5 as central axes in response to voltage application to the movable electrodes 3a and 3b and the movable electrodes 3c and 3d.

The construction of the optical scanning element disclosed in JP-A-11-52278 is shown in FIG. 23. This optical scanning element 1C is generally called a comb electrode structure. Specifically, the interelectrode distance is small, and the opposing area between the electrodes is wide, so that the drive voltage can be made lower. In addition, fixed electrodes 6a and 6b are not present in the displacement direction (the vertical direction in the figure) of the movable portion 2, so that a pull-in phenomenon for adsorbing the movable portion 2 by the fixed electrodes 6a and 6b does not occur, and the scanning angle can be widened.

The optical scanning element disclosed in JP-A-2001-311900 is shown in FIGS. 24A-24D. FIG. 24A is a front view of the entire optical scanning device, FIG. 24B is a front view of an electrode substrate, FIG. 24C is a sectional view including drive electrodes, and FIG. 24D is a sectional view showing the shape of a drive electrode portion in a magnified manner. This optical scanning element 1D includes a movable portion 2 supported by the beams 4 provided on the same straight line, a mirror 7, counter electrodes 8a and 8b provided at the positions opposite to the mirror 7, and by generating an electrostatic attractive force between the movable portion 2 and the counter electrodes 8a and 8b, the mirror 7 is oscillated back and forth around the beams 4 as a twist rotation axis. The counter electrodes 8a and 8b are provided on inclined surfaces 9a and 9b which are not in parallel to the mirror 7, and on at least parts of the inclined surfaces, grooves 10 are formed. In the figures, the reference numeral 11 denotes a frame, 12 denotes an electrode pad, and 13 denotes a top of the ridge of the electrode substrate. According to this optical scanning element 1D, the counter electrodes 8a and 8b are provided in an inclined state oppositely to the electrodes of the movable portion 2, and the interelectrode distance is shortened and the voltage is lowered.

The optical element disclosed in JP-A-2002-267995 is shown in FIGS. 25A and 25B. FIG. 25A is a sectional view (P-P section) of the optical scanning element, and FIG. 25B is a plan view. In this optical scanning element 1E, on the end faces inside the frame 14, driving fixed electrodes 15a and 15b are formed so as to face the substrate ends of the mirror 7, and starting fixed electrodes 16a and 16b are formed by deviating them in the substrate thickness direction from the substrate ends of the mirror 7, whereby the substrate of the mirror 7 is stably started with a low voltage. In the figures, the reference numerals 17a and 17b denote electrode pads, and 18a and 18b denote back side electrode pads.

The optical scanning element disclosed in JP-A-2002-328329 is shown in FIG. 26. This optical scanning element 1F is provided with a mirror 7 which reflects incident light forward, a mirror holding substrate 19 which holds the mirror 7, a twist rotative movement shaft 4 which supports the mirror holding substrate 19 so that it can rotatively move, movable electrodes 20 on the side surfaces of the mirror holding substrate 19 supported on the twist rotative movement shaft 4, and fixed electrodes 21 formed at the positions deviated in the thickness direction of the mirror holding substrate 19 from the opposite surfaces 20a of the movable electrodes 20, and the optical scanning oscillation angle is widened and the drive voltage is lowered.

However, the above-described optical scanning elements in the related art have the following problems. That is, the optical scanning elements 1A and 1B of JP-A-2000-310743 are generally driven at a resonant frequency, but the resonant frequency is uniquely determined depending on the structure and materials. Therefore, the structure and materials are designed so as to obtain a desired resonant frequency, but, in the case of high-speed scanning, the movable portion becomes small and the support portion elastic force becomes great, so that the drive voltage and the starting voltage tend to become higher. Particularly, in a medical instrument such as an endoscope, application of a high voltage is not preferable in terms of safety for living bodies. In other words, high-speed driving at a low voltage is demanded. In addition, if a high voltage is applied, this causes a pull-in phenomenon, so that only a part of the interelectrode gap is used as a scanning angle.

The optical scanning element 1C of JP-T-11-52278 is complicated in its comb structure, so that the production process becomes difficult as it is downsized. Further, the comb electrode area is large, so that the entire element area also becomes large, and this is not suitable for downsizing, and in the case of plane scanning of X and Y planes, it becomes difficult to set the second axis spatially.

In the optical scanning element 1D of JP-A-2001-311900, on the side close to the rotation axis where the rotation torque is small, the interelectrode distance is small, but, on the side distant from the rotation axis where the rotation torque is high, the interelectrode distance is not greatly changed. Therefore, when starting the element, the effect of lowering the voltage is small.

In the optical scanning element 1E of JP-A-2002-267995 and the optical scanning element 1F in JP-A-2002-328329, in addition to the drive electrodes, other driving or starting electrodes are provided on the movable portion side surfaces, and by using these second electrodes, the element is driven with a lower voltage, however, according to the increase in the number of electrodes, the structure becomes complicated and is not suitable for downsizing. The second electrodes are added close to the rotation axis, so that the torque becomes small, and similar to the elements described above, the effect of lowering the voltage is small and in the case of plane scanning of X and Y planes, it is difficult to set the second axis.

Along with these problems, the optical scanning elements in the related art have the following problem. That is, as described above, in use for an endoscope, the drive voltage cannot be raised in terms of safety. To lower the voltage, the resonant frequency of the movable portion is lowered, that is, the movable portion is softened. However, if the elasticity of the beams is lowered, the elastic restoring force of the movable portion is reduced, and it becomes difficult to increase the operation speed, and this is not practicable. In use for an endoscope, a frequency of a normal element drive signal (resonant frequency, etc., of the element) can be used, however, to meet the demand for high-speed image taking, etc., to drive the element at a frequency one digit or more higher, the drive voltage must be made higher, and this is not practicable in the conventional driving method.

SUMMARY OF THE INVENTION

An object of the invention is to provide an optical scanning probe and an optical scanning probe device, and a method for controlling the optical scanning probe which realize low-voltage high-speed driving by a simple structure.

The above-described object of the present invention can be achieved by the following constitution.

(1) An optical scanning probe for observing an inside of a subject by scanning and irradiating a region inside the subject with light and detecting light emitted from an irradiated point of the region,
the optical scanning probe comprising:
an optical scanning element that is disposed in a tip end portion of the probe and that optically scans the region inside the subject with light guided to the tip end portion through a light transmitting section inserted in the probe; and
a signal switching section that switches drive signals for making the optical scanning element perform optical scanning,
wherein
the optical scanning element includes: a movable portion having a micro mirror that is supported so as to be elastically displaced and that is displaced bidirectionally in a first rotating direction and a second rotating direction that is a reverse direction of the first rotating direction; a first driver that applies a physical acting force in the first rotating direction to the movable portion; and a second driver that applies a physical acting force in the second rotating direction to the movable portion,
the signal switching section has a function for switching between a scanning preparation signal and a scanning drive signal and outputting the switched signal, wherein the scanning preparation signal is for attracting the movable portion in one of the first rotating direction and the second rotating direction in response to a timing signal before the probe is inserted into the subject, and the scanning drive signal is for attracting the movable portion alternately in the first rotating direction and the second rotating direction, and
a maximum voltage of the scanning preparation signal is set to be higher than a maximum voltage of the scanning drive signal.

According to this optical scanning probe, a driving preparation signal with a high voltage is used only when starting, and the movable portion is attracted to a specific position in the rotating direction. Accordingly, it becomes unnecessary to select a support portion material depending on the applied voltage, and support portions can be made of a material with a great elastic restoring force. After being inserted into a subject, the driving preparation signal is switched to a safe low-voltage scanning drive signal, and high-speed driving (scanning) can be performed while urging driving energy stored in the support portions with a great elastic restoring force in the respective rotating (swing) directions according to alternation of the low-voltage scanning drive signal.

(2) The optical scanning probe described in (1), further comprising a sensor that outputs a detection signal by detecting insertion of the probe into the subject,
wherein the detection signal output from the sensor is input as the timing signal into the signal switching section.

According to this optical scanning probe, when the probe is inserted in a subject, this insertion is detected by a sensor, and an insertion detection signal is input into the signal switching section. The signal switching section into which the insertion detection signal has been input switches a driving preparation signal applied to the optical scanning element for attracting the movable portion to a scanning drive signal with a lower voltage and outputs this signal.

(3) The optical scanning probe described in (1), wherein the timing signal is input into the signal switching section when a power supply to the optical scanning probe is turned on.

According to this optical scanning probe, when the power supply is turned on when starting use of the optical scanning probe, the signal switching section quickly outputs a driving preparation signal to the optical scanning element to attract the movable portion in either the first rotating direction or the second rotating direction. In other words, elastic energy storage preparation before insertion into the subject can be made easily concurrently with the turning-on of the power supply without a special operation.

(4) The optical scanning probe described in (1), wherein the timing signal is input by a switch connected to the signal switching section.

According to this optical scanning probe, by turning-on of the power supply when starting use of the optical scanning probe and manually inputting the signal by the switch connected to the signal switching section, the signal switching section outputs a driving preparation signal to the optical scanning element to attract the movable portion in either the first rotating direction or the second rotating direction. In other words, elastic energy storage preparation before inserting into the subject can be started from a desired time, and wasteful attraction of the movable portion when the element is not inserted for a long period of time after the power supply is turned on, can be prevented.

(5) The optical scanning probe described in any one of (1) through (4), wherein a final displaced position of the movable portion, when a displacement direction of the movable portion is switched between the first rotating direction and the second rotating direction, is a position at which a lower end of the movable portion comes into contact with a member below the movable portion.

According to this optical scanning probe, displacement of the movable portion is in the range up to the final displaced position in the first rotating direction and the final displaced position in the second rotating direction, and the scanning angle of the movable portion is secured to be maximum in the movable range of the movable portion.

(6) The optical scanning probe described in any one of (1) through (4), wherein a final displaced position of the movable portion, when a displacement direction of the movable portion is switched between the first rotating direction and the second rotating direction, is just before a position at which a lower end of the movable portion comes into contact with a member below the movable portion.

According to this optical scanning probe, although the scanning angle of the movable portion is narrow, the degree of freedom of material selection is increased. In addition, electric charge due to repetition of contact and separation of the movable portion in an electrically insulated state with and from the contact surface does not occur, so that variation of driving characteristic and deterioration over time of the optical scanning element can be prevented.

(7) The optical scanning probe described in any one of (1) through (6), wherein the physical acting force is an electrostatic force.

According to this optical scanning probe, driving is performed by using an electrostatic force, so that, for example, the driving state can be easily controlled by switching the voltage to be applied between the fixed side electrodes and the movable side electrodes.

(8) The optical scanning probe described in any one of (1) through (7), wherein the physical acting force is applied to a plurality of points of application of the movable portion.

According to this optical scanning probe, a plurality of points of application are set, so that, for example, physical stresses are applied to both sides of the rotation center of the swing type movable portion whose center is the rotation center. Accordingly, different magnitudes of braking forces can be applied to the respective points of application at different timings, and for example, various braking effects such as urging or attractive holding, etc., in the first rotating direction and the second rotating direction are obtained.

(9) The optical scanning probe described in (8), wherein two or more physical acting forces can be set in each of the first and second rotating directions of the movable portion.

According to this optical scanning probe, two or more physical stresses can be applied to each side of two sides sandwiching the rotation center of, for example, a swing type movable portion whose center is the rotation center. Accordingly, different magnitudes of braking forces can be applied to one side of the movable portion at different timings, and, for example, various braking effects such as braking of the movable portion at a position just before contact by applying an attractive force reverse to the rotating direction can be obtained.

(10) The optical scanning probe described in any one of (1) through (9), further comprising a sealing structure that seals at least the movable portion under a reduced pressure lower than an atmospheric pressure.

According to this optical scanning probe, the movable portion operates in an environment under a reduced pressure lower than the atmospheric pressure, so that the influence of air viscosity can be reduced. In an optical scanning element which is formed to be very small, the movable portion has a small mass, so that when oscillating these at a high speed, they are influenced by viscosity of air around these, and it becomes difficult to raise the oscillation frequency. Therefore, by sealing the movable portion under the reduced pressure, the movable portion oscillates in the air with density lower than normal, so that the influence of air viscosity becomes smaller and high-speed driving is possible.

(11) The optical scanning probe described in any one of (1) through (10), wherein the optical scanning element is supported so that the movable portion can be rotatively displaced biaxially around a first rotation axis for displacement in the first and second rotating directions and a second rotation axis orthogonal to the first rotation axis, and two-dimensionally optically scans the region of the subject.

According to this optical scanning probe, the movable portion is three-dimensionally driven so as to be rotatively displaced around the first rotation axis and the second rotation axis orthogonal to each other, and two-dimensional scanning can be performed by irradiation light and return light, and an image of the irradiated region based on return light distribution information can be formed.

(12) The optical scanning probe described in any one of (1) through (11), further comprising:

a light source that emits light to be irradiated onto the subject;

a scanning driver that supplies a drive signal for driving and swinging the micro mirror of the optical scanning element; and a return light transmitting section that guides light from the irradiation point of the subject of light two-dimensionally scanned by the optical scanning element to a base end portion.

This optical scanning probe two-dimensionally scans light introduced from a light source by using the optical scanning element provided in the optical scanning section, so that a specific region in the subject is irradiated, and light (return light) emitted from this irradiation point is guided to the base end side, whereby a two-dimensional image of the specific region can be detected.

(13) The optical scanning probe described in (12), further comprising a pinhole between the light source and the optical scanning element, wherein light passing through the pinhole substantially becomes a point light source to form a confocal optical system between the light source and the subject.

According to this optical scanning probe, a confocal optical system is constructed, so that when two-dimensionally scanning light by using the optical scanning element, only an optical image of a focused region (scanning position) of an object in the subject can be detected. Irradiation light is irradiated onto the object in the subject via the confocal optical system from the pinhole serving as a point light source, so that the irradiation light is intensively irradiated onto only one focused point. Therefore, undesired scattered light is not generated from the periphery of the scanning position, so that an image of the scanning position can be detected with high contrast. Further, by using the confocal optical system, irradiation light and return light can be guided by using a thin member like an optical fiber, so that a long and thin optical scanning probe preferably usable as an endoscope can be constructed.

(14) The optical scanning probe described in (13), wherein the pinhole is formed in a ferruled attached to an end portion of the light transmitting section at the tip end portion of the probe.

According to this optical scanning probe, a light exit end of the ferrule inside the optical fiber connector attached to the end of the light transmitting section is effectively used as a confocal pinhole forming substantially a point light source.

(15) The optical scanning probe described in any one of (1) through (14), wherein the light emitted from the irradiation point is one of reflected light, scattered light, fluorescence, and phosphorescence.

According to this optical scanning probe, by detecting any of reflected light, scattered light, fluorescence, and phosphorescence emitted from the irradiation point, for example, various diagnoses are possible in medical use.

(16) An optical scanning probe device comprising:
an optical scanning probe described in any one of (1) through (15);
a signal processor that obtains, from return light guided from the return light transmitting section and a drive signal of the scanning driver, one-dimensional or two-dimensional distribution information of the light emitted from the irradiation point inside the subject; and
a display that displays a video signal output from the signal processor.

According to this optical scanning probe device, when light output from the optical scanning probe is scanned, light emitted from the irradiation point of the subject is guided by the return light transmitting section, and the intensity of the return light is output as an electric signal by a photoelectric converting element, etc. The output electric signal is input into the signal processing device and displayed on the display as distribution information of light emitted from the irradiation point.

(17) A method for controlling the optical scanning probe described in any one of (1) through (15), comprising repeating based on the scanning drive signal:
storing a first elastic energy in an elastic support that supports the movable portion, in displacing the movable portion in one direction of the first and second rotating directions;
generating a first physical acting force by one driver of the first and second drivers to displace the movable portion in the one direction;
making the first physical acting force disappear and releasing the first elastic energy stored in the elastic support beam so as to store a second elastic energy having a polarity reverse to that of the first elastic energy in the elastic support beam and to displace the movable portion in the other direction of the first and second rotating directions; and
generating a second physical acting force by the other driver of the first and second drivers to displace the movable portion in the other direction.

According to this method for controlling the optical scanning probe, before the probe is inserted in the subject, the movable portion is inclined by a comparatively high voltage, and elastic energy is stored in the elastic support beam. In this state, application of the high voltage is stopped, and the probe is inserted in the subject. After being inserted in the subject, the movable portion is swung by releasing the elastic energy stored in the elastic support beam, and the swung movable portion is rotated up to the other rotating direction while storing elastic energy in the reverse direction by inertia, and then the movable portion switches into the return direction again at the point in time when the inertia disappears and the balance of the stored elastic force is inverted. This repetition of switching is urged by alternation of a low-voltage scanning drive signal, the elastic energy in the elastic support beam is released and re-stored, and the movable portion continuously swings.

(18) The method for controlling the optical scanning probe described in (17), wherein a maximum voltage of the scanning drive signal is set to be less than 100V.

According to this method for controlling the optical scanning probe, after being inserted in the subject, a scanning drive signal necessary for optical scanning is set to be less than 100V at maximum, whereby the safety in use for an endoscope is secured. This maximum voltage can be further lowered by changing the dimensions and materials of the optical scanning element.

(19) The method for controlling the optical scanning probe described in (17) or (18), wherein the movable portion is displaced with a period corresponding to a resonant frequency of the movable portion.

According to this method for controlling the optical scanning probe, the movable portion is driven so as to swing at a resonant frequency corresponding to an eigen frequency determined according to the shape and the mass etc., of the movable portion, so that efficient driving can be performed with a minimum driving force, and the swing operation becomes stable.

BRIEF DESCRIPTION OF THE DRAWINGS

The features of the invention will appear more fully upon consideration of the exemplary embodiments of the inventions, which are schematically set forth in the drawings, in which:

FIG. 24A is a front view of the entire optical scanning device, FIG. 24B is a front view of the electrode substrate, and FIG. 24C is a sectional view including drive electrodes;

FIG. 25A is a sectional view of the optical scanning element (P-P section), and FIG. 25B is a plan view.

Figure 1:
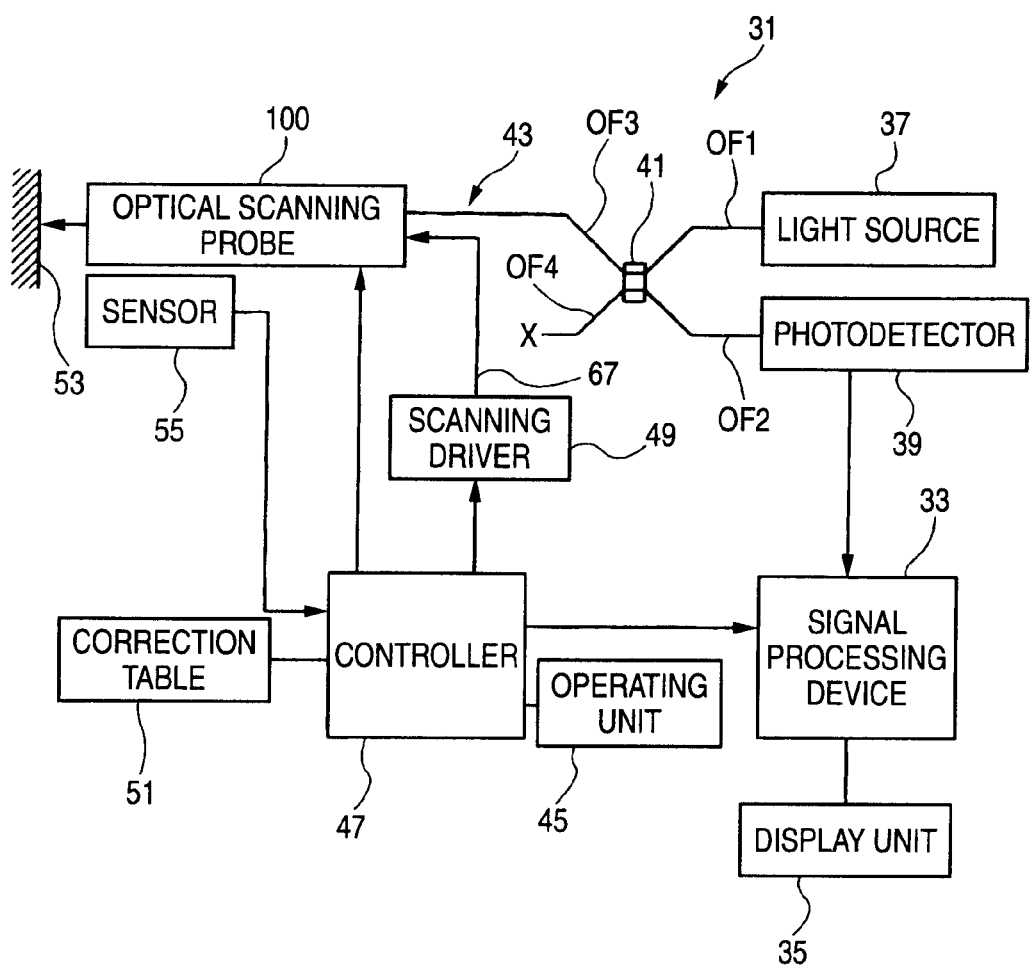
FIG. 1 is a block diagram of an optical scanning probe device including an optical scanning probe according to an exemplary embodiment of the present invention.

30: Endoscope device
31: Optical scanning probe device
33: Signal processing device (signal processor)
35: Display unit
43: Optical fiber (light transmitting means, return light transmitting means)
49: Scanning driver
53: Subject
55: Sensor
71: Ferrule
81: Optical scanning element
83: Micro mirror
95: Movable portion
97: Elastic support beam (first rotation axis, elastic support beam)
100: Optical scanning probe
101a: First driver
101b: Second driver
105: Drive voltage control circuit (signal switching section)
109: Pivot (member below the movable portion)
125: Elastic support beam (second rotation axis, elastic support beam)
V1: Driving preparation signal
V2: Scanning drive signal

DETAILED DESCRIPTION OF THE EXEMPLARY EMBODIMENTS

An optical scanning probe according to an exemplary embodiment of the present invention includes an optical scanning element which scans light across a subject and a signal switching section for switching drive signals for making the optical scanning element scan light, in which the optical scanning element includes a movable portion having a micro mirror which is displaced in the first rotating direction and the second rotating direction and first and second drivers which apply physical acting forces to the movable portion, and the signal switching section has a function for switching from a driving preparation signal for attracting the movable portion in either the first rotating direction or the second rotating direction alternately and outputting this signal, and the maximum voltage of the driving preparation signal is set to be higher than the maximum voltage of the scanning drive signal, so that by using a high voltage only when starting, the voltage can be lowered when driving. The driving increases the effect of the support portion elastic force, and this enables high-speed driving. As a result, low-voltage high-speed driving is realized by a simple structure.

An optical scanning probe device according to an exemplary embodiment of the present invention includes the optical scanning probe, a signal processor which obtains one-dimensional or two-dimensional light distribution information of light emitted from the irradiation point in a subject from return light guided from the return light transmitting section of the optical scanning probe device and a drive signal of the scanning driver, and a display unit which displays video signals output from the signal processor, so that by using the optical scanning probe having the simple structure, the intensity of return light is input as an electric signal into the signal processing device while light-scanning at high speed with a low voltage, and return light distribution information can be displayed on the display unit at a high speed.

According to a method for controlling the optical scanning probe in an exemplary embodiment of the present invention, a scanning drive signal is a drive signal which repeats the process in which elastic energy is stored in the elastic support beam supporting the movable portion until the movable portion is displaced in the one rotating direction and the movable portion is displaced by a physical acting force generated from the one driver, and then the physical acting force from the one driver is made to disappear and the elastic energy stored in the elastic support beam is released, whereby while elastic energy with polarity reverse to that of the aforementioned elastic energy is stored again in the elastic support beam, the movable portion is displaced in the other rotating direction, and the movable portion is displaced by a physical acting force generated from the other driver. Therefore, before the probe is inserted in the subject, the movable portion is inclined with a comparatively high voltage, and from this state, application of the high voltage is stopped, and then the probe is inserted in the subject. After being inserted into the subject, the movable portion is continuously driven with a low voltage. Accordingly, without making the structure complicated and the production process, high-speed scanning and a lower voltage are realized by a simple structure by devising the driving method.

Hereinafter, exemplary embodiments of an optical scanning probe and an optical scanning probe device, and a method for controlling the optical scanning probe of the present invention will be described with reference to the drawings.

FIG. 1 is a block diagram of an optical scanning device having an optical scanning probe according to an exemplary embodiment of the present invention.

The optical scanning probe device 31 includes an optical system for inputting and outputting optical information into and from the optical scanning probe 100 and a drive system for inputting drive control information into the optical scanning probe, and by inputting and outputting information into and from both systems, an observed image is made up to be output to a display unit 35 via a signal processing device 33.

The optical system includes a light source 37 including a semiconductor laser, etc., a photodetector 39, an optical coupler 41, and an optical fiber 43 as a light transmitting section (and return light transmitting section) connecting these members, and the drive system includes an operating unit 45, a controller 47 connected to the operating unit 45, a scanning driver 49, and a correction table 51 (all described later).

A laser beam output from the light source 37 is adjusted in light amount by a proper light amount adjusting unit and guided to a first optical fiber OF1, and branched to a third optical fiber OF3 and a fourth optical fiber OF4 by the optical coupler 41 having four inputs and outputs. The third optical fiber OF3, as a laser beam multiplexed with a visible laser beam, is transmitted to the optical scanning probe 100. Then, by scanning the laser beam by an objective unit described later installed inside the tip end portion of the optical scanning probe 100, observation light (observation beam) is scanned and condensed to an observation point near the surface of the subject 53.

On the other hand, light emitted from an irradiation point at a scanning position on the subject 53 to be detected returns to the optical scanning probe 100 and is guided to the optical coupler 41 via the optical fiber 43. Then, the light branched to the second optical fiber OF2 from the optical coupler 41 is detected by the photodetector 39. The photodetector 39 is a device to output the intensity of incident light as an electric signal like a photoelectric converting element. The electric signal output from the photodetector 39 is input into the signal processing device 33 and displayed on the display unit 35.

To prevent the light branched to the fourth optical fiber OF4 from being reflected by the end of the fourth optical fiber and returning to the optical coupler side 41, the end of the fourth optical fiber OF4 is closed or subjected to non-reflective treatment. As these first optical fiber OF1, second optical fiber OF2, third optical fiber OF3, and fourth optical fiber OF4, preferably, a single-mode fiber, a low-order multimode fiber capable of sufficiently maintaining coherence, or a polarization-preserving fiber etc., can be used.

Then, the controller 47 makes the scanning driver 49 generate a drive signal for performing optical scanning in the objective unit, and outputs this drive signal to the signal processing device 33 and makes this form an image and perform a freeze operation for a taken image or hard copying of a still image, and control various operations such as bending of the optical scanning probe 100 in response to an operation signal from the operating unit 45.

A sensor 55 is connected to the controller 47, and the sensor 55 detects that the probe has been inserted into the subject 53 and outputs a detection signal. The detection signal output from the sensor 55 is input as a timing signal described later into a drive voltage control circuit 105 (see FIG. 5) that is a signal switching section.

Next, a state where the optical scanning probe device 31 is incorporated in an endoscope device will be described.

Figure 2:
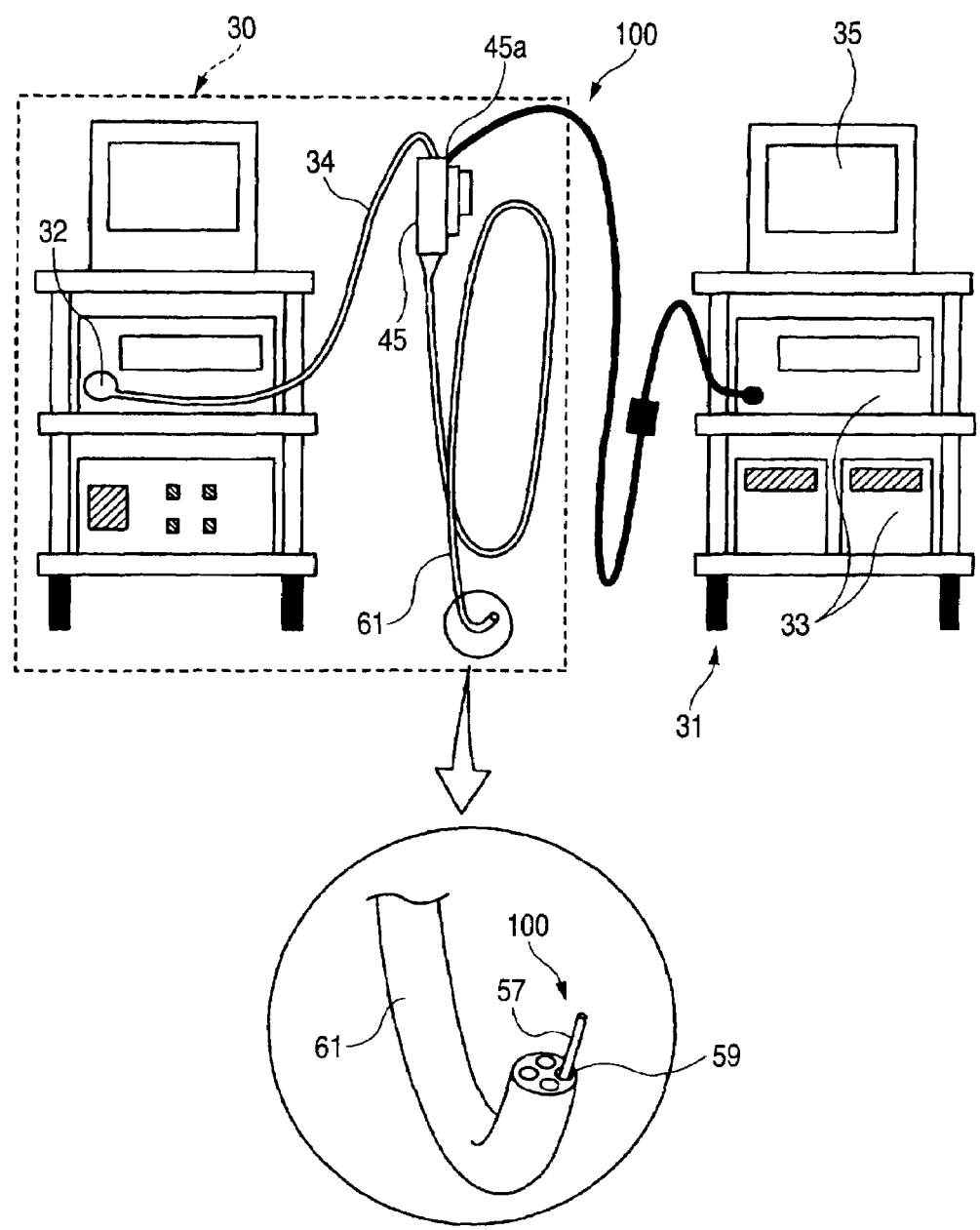
FIG. 2 is a front view showing the entire construction of an optical scanning probe device including an optical scanning probe equipped with an optical scanning element and an endoscope device.

FIG. 2 is a front view of a construction of an optical scanning probe device including an optical scanning probe equipped with an optical scanning element and the entirety of an endoscope device.

The optical scanning probe 100 is inserted at its tip end portion into the subject 53, irradiates light onto a region inside the subject 53 while scanning, and observes the inside of the subject 53 by detecting light emitted from the irradiation point. This optical scanning probe 100 is covered with a sheath 57 that is long and thin and has flexibility.

To a connector 32 of the endoscope device 30, the base end side of a scope 34 is connected, and to the other end side of this scope 34, an operating unit 45 is connected. To the tip end of the operating unit 45, a long and thin inserting portion 61 is connected. The operating unit 45 is provided with a forceps insertion opening 45a, and from this insertion opening 45a, the optical scanning probe 100 is inserted. The optical scanning probe 100 is extended to the tip end of the inserting portion 61 via a forceps inlet 59 formed in the inserting portion 61.

The optical scanning probe device 31 includes, as shown in FIG. 1, the optical scanning probe 100, the signal processing device 33 which obtains one-dimensional or two-dimensional distribution information of light emitted from an irradiation point in a region inside the subject 53 from return light guided from the optical fiber 43 of the optical scanning probe 100 and the drive signal of the scanning driver 49, and a display unit 35 which displays video signals output from the signal processing device 33, and when light output from the optical scanning probe 100 is scanned, light emitted from the subject 53 is guided as return light by the optical fiber 43, and the intensity of the return light is output as an electric signal by a photoelectric converting element, etc. The output electric signal is input into the signal processing device 33 and becomes distribution information of light emitted from the irradiation point and is displayed on the display unit 5.

Herein, light emitted from the irradiation point (return light) includes any of reflected light, scattered light, fluorescence, and phosphorescence from the light irradiated region, and by detecting these light components, various diagnoses are possible. Scattered light is used to calculate an attenuation rate from a ratio of the scattered light to reflected light, and further obtain oxygen metabolism based on the attenuation rate at each wavelength, and so on. Fluorescence is used for diagnosis from image information based on fluorescence emitted from light-sensitive substances by irradiating excitation light onto a portion inside a living body absorbing the light-sensitive substances which emit fluorescence, and is generally used for photodynamic diagnosis generally referred to as PDD. When a lesion at which a photosensitizer is specifically accumulated is irradiated with a laser, active oxygen emits phosphorescence. By imaging this phosphorescence, the infiltrated state of the lesion, the range of the lesion, and the lesion can be diagnosed.

Figure 3:
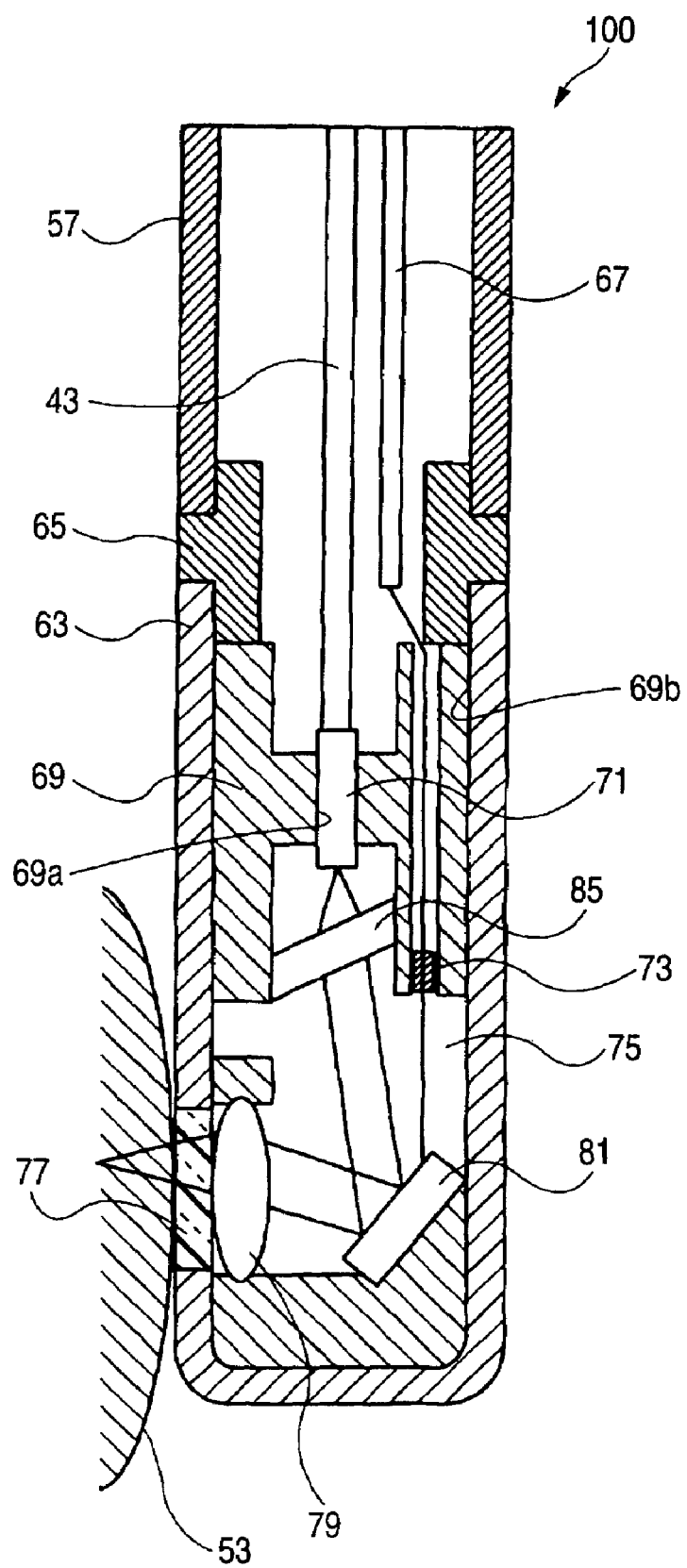
FIG. 3 is a sectional view showing the structure of a tip end portion of the optical scanning probe.

Next, a sectional view showing a structure of the tip end portion of the optical scanning probe device is shown in FIG. 3.

In the optical scanning probe 100, a tip end frame 63 is connected to the tip end of the sheath 57 via a ring-shaped joint 65, and the optical fiber 43 and a signal line 67 inserted in the sheath 57 are connected to the tip end frame 63 side. The tip end frame 63 has a cylindrical structure whose tip end portion is closed.

Inside the tip end frame 63, a holding member 69 is held in an external shape substantially equivalent to the inner diameter of the tip end frame 63, and in the holding member 69, communicating holes 69a and 69b for insertion of the optical fiber 43 and the signal line 67 are formed. In the communicating hole 69a, a ferrule 71 provided on the tip end of the optical fiber 43 is disposed, and in the communicating hole 69b, the signal line 67 is inserted together with a packing 73, whereby at the internal area of the tip end frame 63, a sealed internal space 75 is defined by the holding member 69.

At a part near the tip end of the tip end frame 63, an opening for imaging the subject 53 is formed, and a cover glass 77 is attached to this opening portion. At a position adjacent to this cover glass 77, a condenser lens 79 is disposed, and the optical scanning element 81 is disposed so as to face the condenser lens 79. The optical scanning element 81 is set in a state inclined by about 45 degrees with respect to the axial direction of the tip end frame 63, and the light path of incident light is changed by a micro mirror 83 (see FIG. 4) which can be rotatively displaced as described later. In other words, light output from the ferrule 71 fixed to the holding member 69 is irradiated onto the optical scanning elements via a collimator lens 85 supported by the holding member 69, and reflected light thereof is scanned and irradiated onto the subject 53.

Herein, electrodes to which a drive signal (corresponding to Va, Vb described later) is applied for driving the optical scanning element 81 for scanning are connected to the scanning driver 49 (see FIG. 1) via the signal line 67.

The ferrule 71 disposed at a position penetrating through the center of the holding member 69 has a micro through hole penetrating the center, and to one end thereof, the optical fiber 43 is connected, and the opening on the other end side is free. Therefore, the optical system of the optical scanning probe 100 shown in FIG. 1 composes a confocal optical system, and the ferrule 71 functions as a confocal pinhole. Irradiation light is input into the optical fiber 43 from the light source 37 (see FIG. 1), and output as irradiation light of a point light source from the opening of the ferrule 71. This irradiation light is converted into parallel light by the collimator lens 85 and made incident on the surface of the micro mirror 83 of the optical scanning element 81, and is reflected by the surface of the micro mirror 83, condensed by the condenser lens 79, and is irradiated onto the subject 53 via the cover glass 77.

On the other hand, in the region of the subject 53, reflected light from a point corresponding to a scanning position determined according to the inclination of the surface of the micro mirror 83 of the optical scanning element 81 follows the path in reverse passes through the cover glass 77, and is condensed by the condenser lens 79 and guided to the micro mirror 83 of the optical scanning element 81, reflected by the surface of the micro mirror 83, and made incident on the opening portion of the ferrule 71 as a confocal pinhole via the collimator lens, and guided to the optical detector 39 (see FIG. 1) via the optical fiber 43. In other words, the optical fiber 43 also serves as a return light transmitting section.

In this confocal optical system, by disposing a pinhole having a circular opening at a position (image position) conjugate to the focal position of the condenser lens 79, light of only the focused position can be detected. In the present embodiment, the light exit end of the ferrule 71 attached to the end of the optical fiber 43 is effectively used as a confocal pinhole forming substantially a point light source. In the confocal optical system, light outgoing from the point light source is condensed and irradiated onto one point of the subject 53 by the objective lens. Therefore, different from general illumination which equally illuminates the entire subject 53, undesired scattered light from the periphery of the scanning position is not produced, and the image contrast is greatly improved. Further, by using the confocal optical system, irradiation light and return light can be guided by using a thin member like the optical fiber 43, so that a long and thin optical scanning probe 100 preferably usable as the optical scanning probe device 31 can be formed. Therefore, the surface of the inside of the subject such as the inside of living body tissue, etc., can be observed as a high-quality image.

When taking the above-described image, the controller 47 (see FIG. 1) grasps the timing of each scanning control signal generated by the scanning driver 49, that is, the scanning position of the micro mirror 83 of the optical scanning element 81, and makes the signal processing device 33 process an electric signal input from the photodetector 39 according to this scanning position, and makes the display unit 35 output two-dimensional image information as a taken image of the subject 53.

The inclination angle of the micro mirror 83 of the optical scanning element 81 which determines the scanning range (range to be imaged) changes according to the level of the drive voltage to be applied to each electrode of the optical scanning element 81, but, if interelectrode distances, etc., of optical scanning elements 81 are not uniform, even when the same drive voltage is applied, errors occur in the actual scanning range of each optical scanning element 81. The scanning range may also change according to the influence of environmental changes in temperature, etc.

Therefore, to stabilize the actual scanning range of the optical scanning element 81, the controller 47 has a correction table 51 for correcting a drive voltage to be applied to the optical scanning element 81. In other words, information showing the relationship between the drive voltage value to be applied and the actual inclination angle is registered and held in the table in advance, and when driving the optical scanning element 81 in actuality, a drive voltage value to be applied is determined by referring to the contents of the correction table 51 so that the scanning range is as predetermined.

This correction table 51 is created until shipment of the product of the optical scanning probe device 31. It is also allowed that the contents of the correction table 51 are made rewritable, and the contents of the correction table 51 are rewritten at the time of periodic maintenance. Alternatively, the contents of the correction table 51 may be upgraded at an arbitrary timing determined by a user such as the time of turning-on of the power supply of the optical scanning probe device 31 as appropriate.

In the case that the correspondence relationship between the scanning timing and the actual scanning position, when driving the optical scanning element 81, is nonlinear, information showing this relationship is also registered in the correction table 51.

Figure 4:
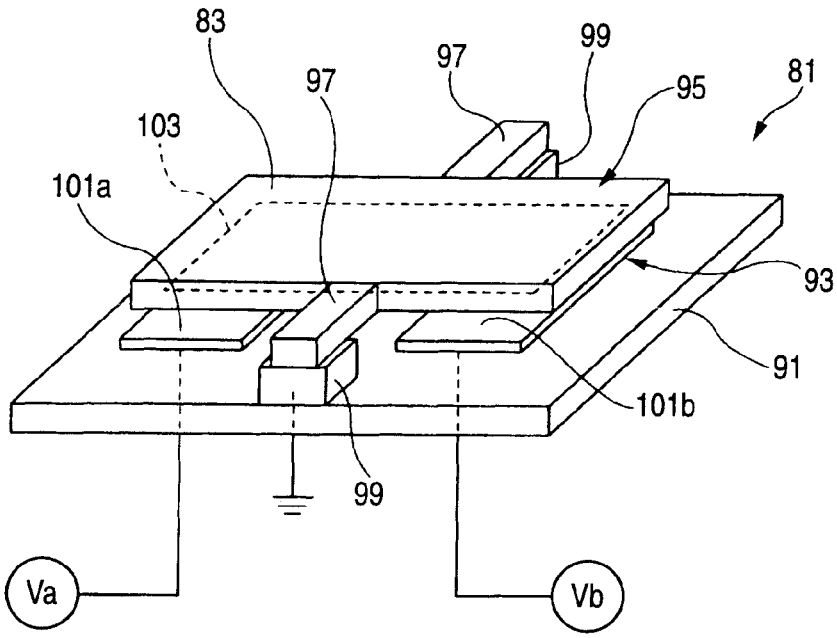
FIG. 4 is a perspective view of the optical scanning element shown in FIG. 3.

FIG. 4 is a perspective view of the optical scanning element shown in FIG. 3.

The optical scanning element 81 is installed in the tip end portion of the optical scanning probe 100 (see FIG. 3), and optically scans a region of the subject 53 with light guided to the tip end portion via the optical fiber 43 inserted in the optical scanning probe 100. The optical scanning element 81 includes, as basic components, a substrate 91, a movable portion 95 formed like a small piece arranged in parallel to the substrate 91 via a gap 93, elastic support beams 97 as support portions extended from both edges of the movable portion 95, and spacers 99 supporting the movable portion 95 on the substrate 91 via the elastic support beams 97. With this construction, the movable portion 95 can be rotatively displaced bidirectionally in a first rotating direction and a second rotating direction reverse to the first rotating direction according to twisting of the elastic support beams 97.

In the optical scanning element 81, the upper surface of the movable portion 95 becomes a micro mirror 83. On the upper surface of the substrate 91, on both sides of the two elastic support beams 97, a first driver 101a which applies a physical acting force in the first rotating direction to the movable portion 95 and a second driver 101b which applies a physical acting force in the second rotating direction to the movable portion 95 are provided. The first driver 101a and the second driver 101b become address electrodes as fixed electrodes. A part of the movable portion 95 is also provided with a movable electrode 103.

Figure 5:
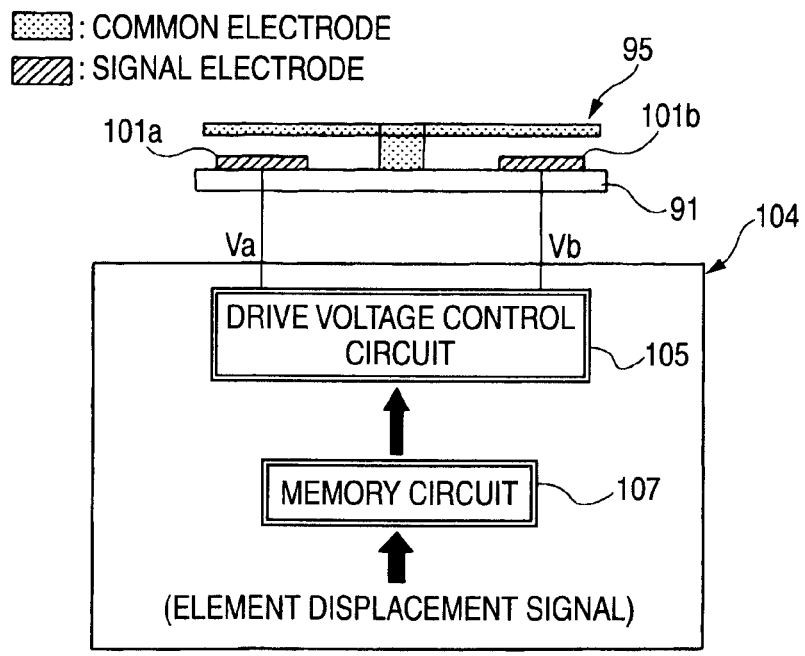
FIG. 5 is a block diagram showing an optical scanning element and an electric circuit for driving the optical scanning element.

FIG. 5 is a block diagram showing the optical scanning element and an electric circuit for driving the optical scanning element.

The optical scanning element 81 includes a drive circuit 104 inside the substrate 91. The drive circuit 104 includes a drive voltage control circuit 105 and a memory circuit 107. The drive voltage control circuit 105 generates drive signals Va and Vb to be applied to the respective electrodes of the optical scanning element 81. The memory circuit 107 holds information of signal waveforms that should be output as each drive signal Va, Vb by associating these with inclination displacement amounts of the micro mirror 83 of the optical scanning element 81 with respect to the respective axes prior to driving of the optical scanning element. When a displacement amount instruction is input from the outside into the memory circuit 107, the memory circuit 107 supplies information necessary for generating signal waveforms corresponding to the displacement amounts to the drive voltage control circuit 105. The drive voltage control circuit 105 generates a waveform of each drive signal Va, Vb at a necessary timing based on information input from the memory circuit 107.

A conductive region formed on the movable portion 95 forms the movable electrode 103 as a common electrode, and by applying voltages to the first driver 101a and the second driver 101b arranged at positions facing the movable electrode, electrostatic forces which become driving forces can be generated.

Herein, a contact driving method in which the movable portion 95 of the optical scanning element 81 is brought into contact with the substrate 91 side and swung will be described.

FIGS. 6A-6F are operation explanatory views showing displaced states of the movable portion 95 of the optical scanning element 81 in contact driving.

The optical scanning element 81 swings and displaces the movable portion 95 around the elastic support beams 97 as a twist center by applying voltages to the first driver 101a, the second driver 101b, and the movable electrode 103 (described as a movable portion 95 in the figures) as basic operations. Accordingly, the micro mirror 83 on the movable portion 95 is swung, and the light reflection direction is switched. However, when starting, the minimum energy for rotatively displacing the movable portion 95 in a balanced state is greater than the energy necessary after starting displacement, and accordingly, the applied voltage of the drive signal should be increased. In the present embodiment, the applied voltage when starting is defined as V1 and the applied voltage in steady driving after starting is defined as V2 (<V1).

Figure 6A:
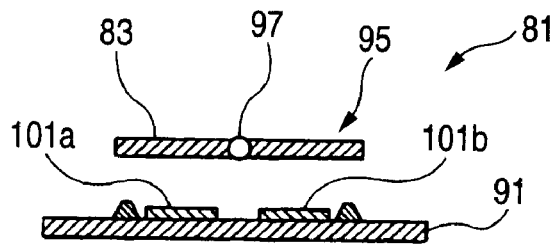
FIGS. 6A-6F are operation explanatory views showing displaced states of the movable portion in contact driving.
Figure 6B:
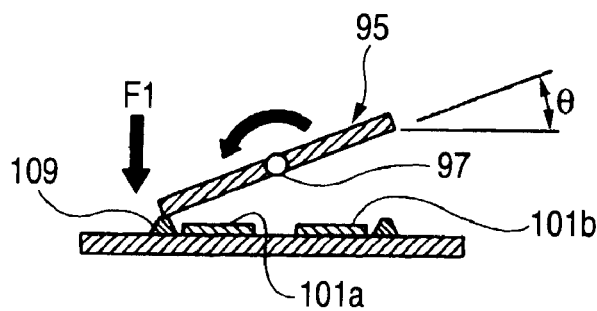

To bring the movable portion 95 into contact with the lower portion from the balanced state, as shown in FIG. 6A, from the balanced stop state of the movable portion 95, as shown in FIG. 6B, an electrostatic force F1 acts in response to application of the applied voltage Va (V1) to the first driver 101a to rotatively displace the movable portion 95 and bring it into contact with a pivot 109 set on the substrate 91. The pivot 109 has a function for preventing adhesion to the movable portion 95 in this pull-in state.

Figure 6C:
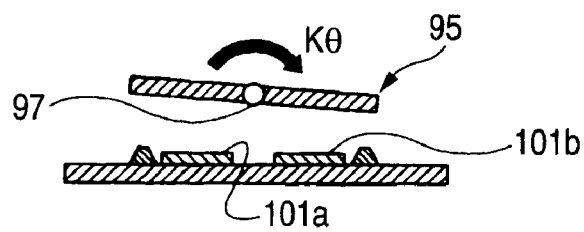

Then, as shown in FIG. 6C, when the applied voltage Va to the first driver 101a is cut off, by the elastic restoring force Kθ of the elastic support beams 97, the movable portion 95 is rotatively displaced in the reverse direction. Thereafter, the driving becomes steady driving and the movable portion 95 continuously swings.

Figure 6D:
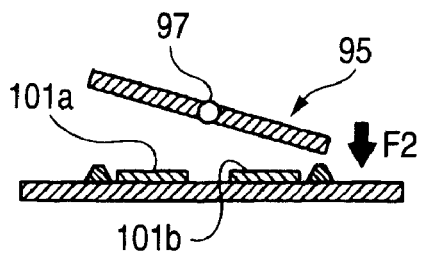

However, as shown in FIG. 6D, when there is no viscosity effect, the movable portion 95 is rotatively displaced to the maximum displaced position, however, when there is a viscosity effect, this displacement becomes smaller. Therefore, to compensate for the shortage of displacement, a voltage V2 lower than the applied voltage value V1 described above is applied as an applied voltage Vb in a pulsed manner to the second driver 101b to generate an electrostatic force F2 (>F1). Herein, the voltage is applied to a degree without causing the second driver 101b to pull-in.

Figure 6E:
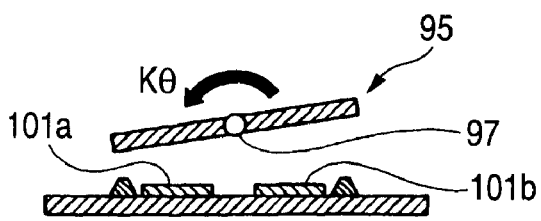
Figure 6F:
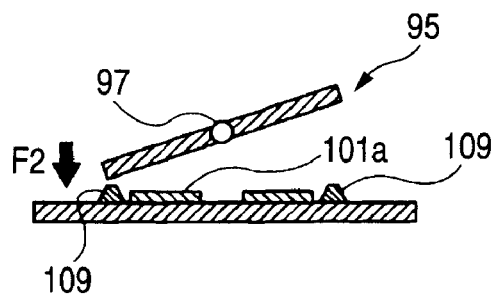

As shown in FIG. 6E, when the applied voltage Vb to the second driver 101b is cut off, the movable portion 95 is rotatively displaced in the reverse direction by the elastic restoring force Kθ of the elastic support beams 97 again. Herein, to compensate for the shortage of displacement again, as shown in FIG. 6F, the applied voltage V2 (<V1) is applied in a pulsed manner to the first driver 101a to generate an electrostatic force F2 (>F1). By repeating the operations of FIG. 6C through FIG. 6F, the movable portion 95 repeatedly swings.

The movable portion 95 is preferably displaced with a period corresponding to the resonant frequency of the movable portion 95. By driving the movable portion 95 at a resonant frequency corresponding to the eigen frequency determined according to the shape and mass, etc., of the movable portion 95, efficient driving is possible with a minimum driving force, and the swing operation is stabilized. When the applied physical acting force becomes an electrostatic force, the movable portion 95 can be rotatively displaced at a high speed. The physical acting force is an electrostatic force, so that, for example, by switching the voltage to be applied between the fixed side electrode and the movable side electrode, the driving state can be easily controlled.

Figure 7:
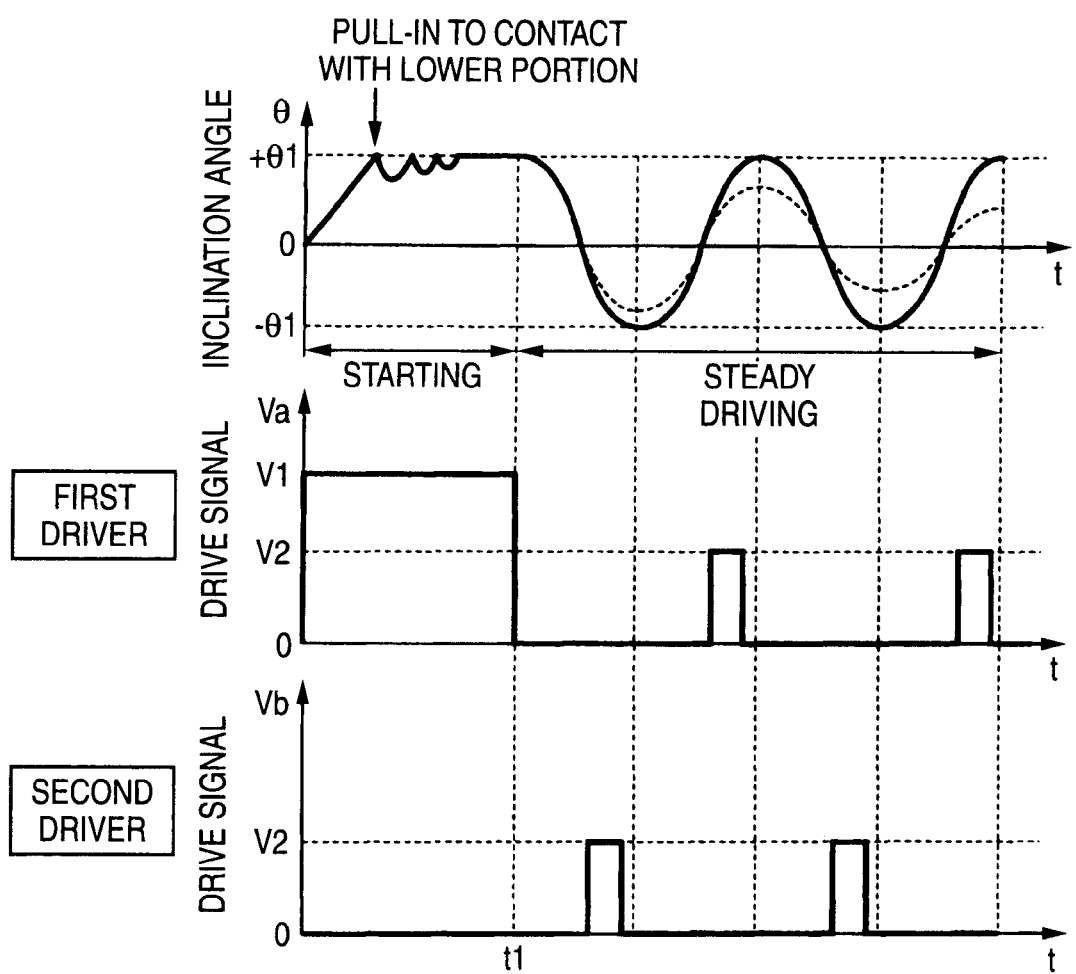
FIG. 7 is an operation explanatory view showing the relationship between the applied voltages and the displacement angle in contact driving.

FIG. 7 is an operation explanatory view showing the relationship between the applied voltage and the displacement angle in contact driving.

Herein, inclination angle changes according to driving of the movable portion 95 shown in FIGS. 6A-6F are described along with drive signals supplied to the first driver 101a and the second driver 101b.

In the case of starting for bringing the movable portion 95 into contact with the lower portion from the balanced state, an inclination angle of the movable portion 95 when the movable portion 95 is brought into contact with the lower portion (the state shown in FIG. 6B) is defined as +θ1. To hold this state, the applied voltage Va is set to the voltage V1 higher than V2. Then, when shifting to steady driving shown in FIG. 6C through FIG. 6F, at this shifting timing t1, the applied voltage Va is changed from V1 to 0. Then, by applying an electrostatic force forward immediately before the movable portion 95 reaches the final displaced position, the movable portion 95 is attracted to the final displaced position. When the movable portion 95 exceeds the final displaced position, without applying an electrostatic force, rotative displacement in the reverse direction is started by the elastic restoring force of the elastic support beams 97. Therefore, the drive signals to the first driver 101a and the second driver 101b in steady driving apply the voltage V2 in a pulsed manner immediately before an inflection point of the swing cycle of the movable portion 95. The waveform of the dotted line in the figure shows a state where the inclination angle range narrows when the viscosity effect occurs. In the present embodiment, a drive signal of the voltage value V2 is applied to the first driver 101a and the second driver 101b to prevent the inclination angle range from narrowing.

Thus, when the lower end of the movable portion 95 is a position which comes into contact with the pivot 109 below the movable portion 95, the displacement of the movable portion 95 is in the range from the final displaced position in the first rotating direction to the final displaced position in the second rotating direction, and the scanning angle of the movable portion 95 is secured to be maximum in the movable range of the movable portion.

Herein, as described above, switching of the drive signal between starting and steady driving will be described in more detail.

In the optical scanning probe device 31 of the present embodiment, the voltage usable in the optical scanning probe 100 has an upper limitation in terms of safety. Therefore, only when starting, a high voltage V1 is applied, and thereafter, a voltage V2 smaller than the voltage V1 is applied for continuous swing. As the voltage values, V2 is smaller than V1, but, in terms of electrostatic force, as shown in FIG. 7, the interelectrode distance at the application timing of the voltage V2 is shorter than the interelectrode distance at the application timing of the voltage V1, and accordingly, the voltage V2 can generate a greater electrostatic force, and the attracting effect of the movable portion 95 can be increased.

As detailed operation procedures, before the probe of the optical scanning probe 100 is inserted into the subject 53, the movable portion 95 is inclined to either one driver from the balanced state by a comparatively high voltage V1, and from this inclined state, application of the high voltage V1 is stopped. Thereafter, the optical scanning probe 100 is inserted into the subject 53. When the probe is inserted into the subject 53, it is driven with a low voltage. Therefore, inside the subject 53, the optical scanning element 81 is not driven with a high voltage.

The timing t1 (see FIG. 7) of changing from the high-voltage to low-voltage driving is controlled by the drive voltage control circuit 105 (see FIG. 5) as a signal switching section. In other words, the controller 47 (see FIG. 1) can change the drive signal for making the optical scanning element 81 perform optical scanning. In detail, the drive voltage control circuit 105 has a function for switching and outputting a scanning drive signal for attracting the movable portion 95 in the first rotating direction and the second rotating direction alternately from the driving preparation signal for attracting the movable portion 95 in either the first rotating direction or the second rotating direction upon receiving a timing signal of the timing t1 from the controller 47 before the probe is inserted into the subject 53. As described above, the maximum voltage of the driving preparation signal is set to be higher than the maximum voltage of the scanning drive signal.

Herein, the scanning drive signal is a drive signal which repeats the process in which elastic energy is stored in the elastic support beams 97 supporting the movable portion 95 until the movable portion 95 is displaced in the one rotating direction, and the movable portion 95 is displaced by a physical acting force generated by the one driver (for example, the first driver 101a), and thereafter the physical acting force from the one driver is made to disappear and the elastic energy stored in the elastic support beams 97 is released, whereby while re-storing elastic energy with polarity reverse to that of the aforementioned elastic energy in the elastic support beams 97, the movable portion 95 is displaced in the other rotating direction, and the movable portion 95 is displaced by a physical acting force generated by the other driver (for example, the second driver 101b).

Thus, in the optical scanning probe device 31, before the probe of the optical scanning probe 100 is inserted into the subject 53, the movable portion 95 is inclined in response to a comparatively high voltage driving preparation signal, and elastic energy is stored in the elastic support beams 97. In this state, application of the high voltage driving preparation signal V1 is stopped, and then the probe is inserted into the subject 53. After stopping the application of the driving preparation signal, the movable portion 95 is rotatively displaced by releasing the elastic energy stored in the elastic support beams 97, and the movable portion 95 rotatively displaced is rotated up to the other rotating direction while storing elastic energy in the reverse direction by inertia, and thereafter, at the point in time when the inertia disappears and the balance of the stored elastic energy is inverted, the movable portion 95 is switched to the return direction again. Repetition of this switching is applied alternately and urged by a low-voltage scanning drive signal, whereby the elastic energy in the elastic support beams 97 is released and stored again, and accordingly, the movable portion 95 continuously swings.

The maximum voltage of the scanning drive signal V2 is preferably set to be less than 100V. When the subject 53 is a human body, after the probe is inserted into the body, a scanning drive signal necessary for optical scanning is set to be less than 100V at maximum, whereby the safety in the use for an endoscope is further secured. This maximum voltage can be further lowered by changing the dimensions and materials of the optical scanning element 81.

The optical scanning probe device 31 of the present embodiment includes a sensor 55 (see FIG. 1) which outputs a detection signal by detecting insertion of the optical scanning probe 100 into the subject 53. The detection signal output from the sensor 55 is input as a signal of timing t1 into the drive voltage control circuit 105 via the controller 47. When the optical scanning probe 100 is inserted into the subject 53, the insertion is detected by the sensor 55, and an insertion detection signal is input into the drive voltage control circuit 105. The drive voltage control circuit 105 into which the insertion detection signal was input switches the driving preparation signal applied to the optical scanning element 81 for attracting the movable portion 95 to a lower-voltage scanning drive signal and outputs this.

In addition, the signal of the timing t1 may be input into the drive voltage control circuit 105 when the power supply to the optical scanning probe 100 is turned on. When the power supply is turned on at the time of starting use of the optical scanning probe 100, the drive voltage control circuit 105 automatically outputs a driving preparation signal to the optical scanning element 81 to attract the movable portion 95 in either the first rotating direction or the second rotating direction. In other words, elastic energy storage preparation before inserting the probe into the subject 53 can be made easily concurrently with the turning-on of the power supply without a special operation.

The signal of the timing t1 may be input by a switch of the operating unit 45 connected to the controller 47. In this case, when starting use of the optical scanning probe 100, the power supply is turned on and a switch connected to the drive voltage control circuit 105 is manually input, whereby the drive voltage control circuit 105 outputs a driving preparation signal to the optical scanning element 81 to attract the movable portion 95 in either the first rotating direction or the second rotating direction. In other words, elastic energy storage preparation before inserting the probe into the subject 53 can be started from a desired time, and wasteful attraction of the movable portion 95 when the probe is not inserted for a long period of time after the power supply is turned on, can be prevented.

As described above, in the optical scanning probe 100 of the present embodiment, only when starting, a driving preparation signal with a high voltage is used and the movable portion 95 is attracted to a position in either one rotating direction. After inserting the probe into the subject 53, the driving preparation signal is switched into a low-voltage scanning drive signal that is safe, and it becomes possible to perform high-speed scanning driving while urging driving energy stored in the elastic support beams 97 with a great elastic restoring force in the respective rotating (swing) directions according to alternation of the low-voltage scanning drive signal.

Next, a non-contact driving method in which the movable portion 95 of the optical scanning element 81 is swung without contact with the substrate 91 side will be described.

FIGS. 8A-8F are operation explanatory views showing displaced states of the movable portion in the case of non-contact driving.

Figure 8A:
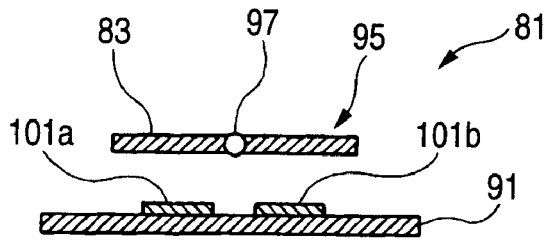
FIGS. 8A-8F are operation explanatory views showing displaced states of the movable portion in non-contact driving.
Figure 8B:
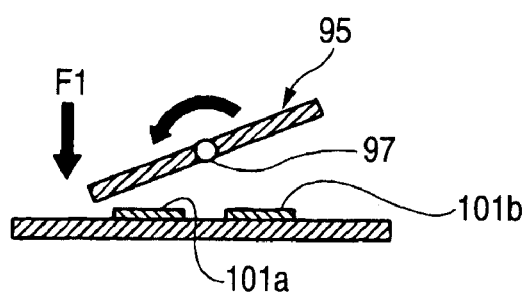

When the movable portion 95 is not brought into contact with the lower portion from the balanced position, an electrostatic force F1 acts by applying an applied voltage Va (V1) to the first driver 101a as shown in FIG. 8B from the balanced stop state of the movable portion 95 shown in FIG. 8A, and the movable portion 95 is rotatively displaced and stopped at a position which is not in contact with the lower portion. In other words, without pulling-in the movable portion 95, it stands still at a middle position.

Figure 8C:
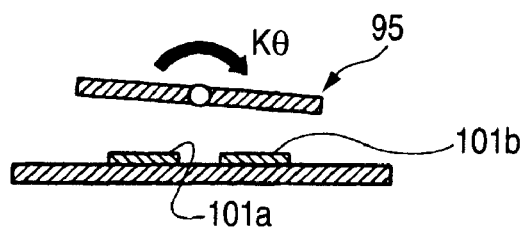

Then, as shown in FIG. 8C, when the applied voltage Va to the first driver 101a is cut off, the movable portion 95 is rotatively displaced in the opposite direction by the elastic force Kθ of the elastic support beams 97. Thereafter, the driving turns into steady driving and the movable portion 95 continuously swings.

Figure 8D:
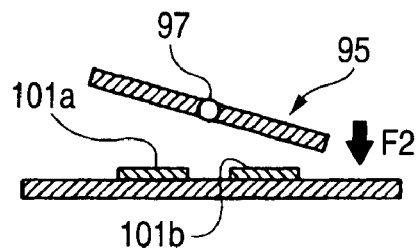

However, as shown in FIG. 8D, when there is no viscosity effect, the movable portion 95 is rotatively displaced to the maximum displaced position, however, when there is a viscosity effect, this displacement is smaller. Therefore, to compensate for the shortage of displacement, the voltage V2 lower than the applied voltage V1 is applied as an applied voltage Vb in a pulsed manner to the second driver 101b to generate an electrostatic force F2 (>F1). Herein, the movable portion 95 is not pulled-in, either.

Figure 8E:
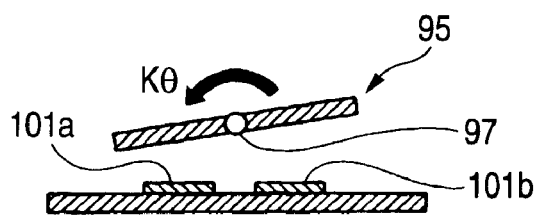
Figure 8F:
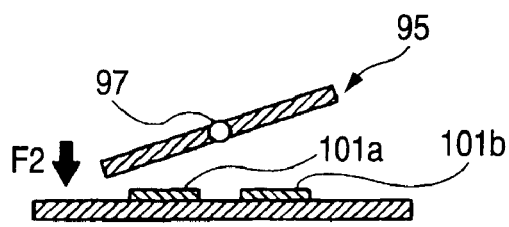

Then, as shown in FIG. 8E, when the applied voltage Va to the second driver 101b is cut off, the movable portion 95 is rotatively displaced in the reverse direction by the elastic force Kθ of the elastic support beams 97 again. Herein, to compensate for the shortage of displacement again, as shown in FIG. 8F, the applied voltage V2 (<V1) is applied to the first driver 101a in a pulsed manner to generate an electrostatic force F2 (>F1). By repeating the operations of FIG. 8C through FIG. 8F, the movable portion 95 repeatedly swings without contact with the lower portion.

The movable portion 95 is preferably displaced with a period corresponding to the resonant frequency of the movable portion 95, and as described above, efficient driving is possible with a necessary minimum driving force, and the swing operation becomes stable.

Figure 9:
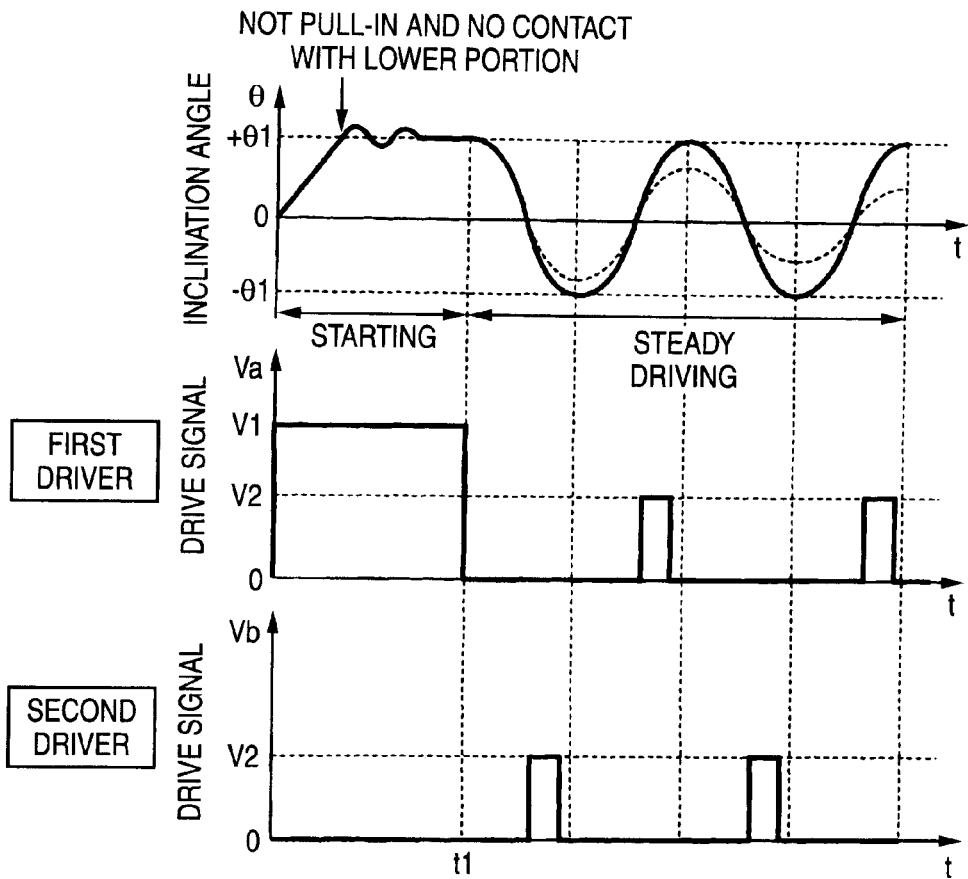
FIG. 9 is an operation explanatory view showing the relationship between the applied voltages and the displacement angle in non-contact driving.

FIG. 9 is an operation explanatory view showing the relationship between the applied voltages and the displacement angle in non-contact driving.

Herein, the inclination angle change according to driving of the movable portion 95 shown in FIGS. 8A-8F is also described along with the drive signals to the first driver 101a and the second driver 101b.

In the case of driving without contact of the movable portion 95 with the lower portion from the balanced position, the maximum displacement angle with which the movable portion 95 does not come into contact with the lower portion is defined as +θ2. To maintain this state, the applied voltage Va is set to the voltage V1 higher than V2.

Thus, when the final displaced position of the movable portion 95 is a position just before coming into contact with the lower member below the movable portion 95, the scanning angle of the movable portion 95 is narrow, but, it is not necessary to consider adhesion to the pivot, so that the degree of freedom in material selection of the element is increased. In addition, electric charge due to repetition of contact and separation of the movable portion in an electrically insulated state with and from the substrate side does not occur, so that driving characteristic scattering and deterioration over time of the optical scanning element 81 are prevented.

Next, a detailed structure example of the optical scanning element and results of analysis through simulation of the operations of the optical scanning element will be described.

Figure 10:
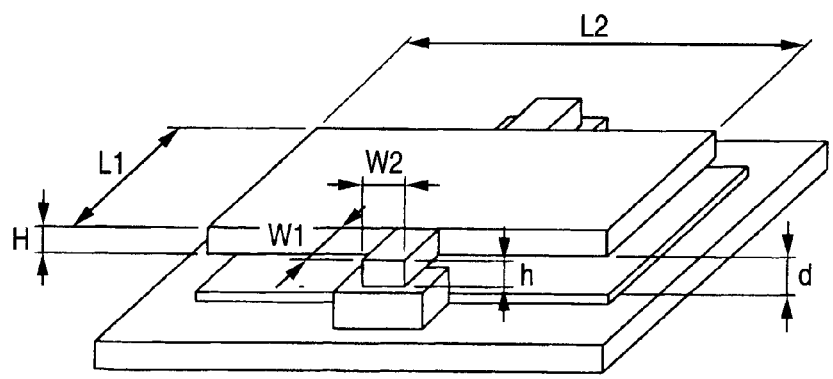
FIG. 10 is a perspective view showing the structure of the optical scanning element used for structure analysis.
Figure 11:
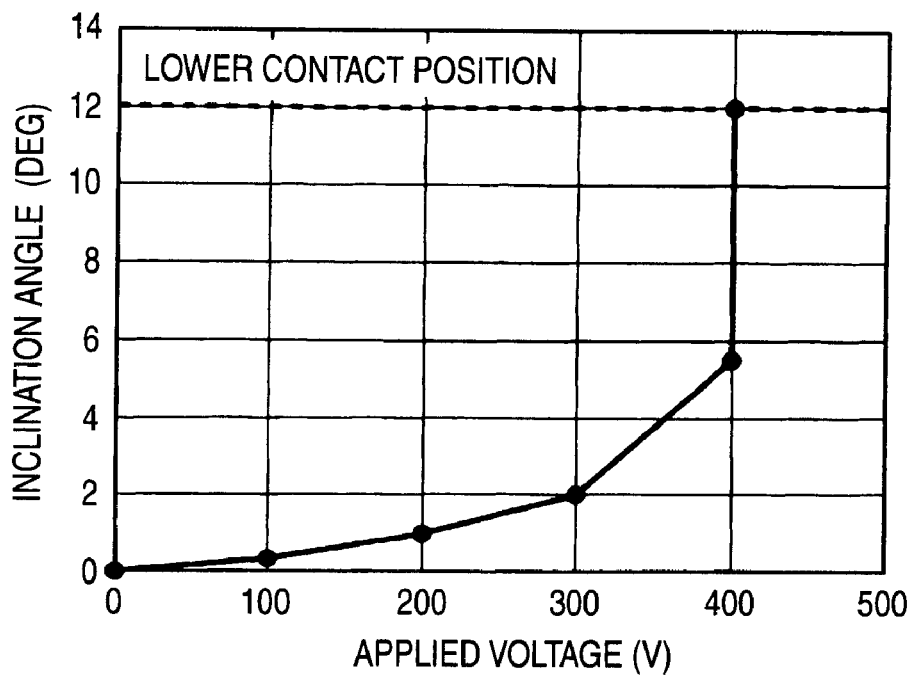
FIG. 11 is a correlation diagram between the rotation angle and applied voltage as analysis results obtained by using the analytical model shown in FIG. 10.

FIG. 10 is a perspective view showing a structure of an optical scanning element used for structure analysis, and FIG. 11 is a correlation diagram of the inclination angle of the movable portion and the applied voltage, showing analysis results obtained by using the analytical model shown in FIG. 10.

The sizes of the optical scanning element were assumed in actuality, and static analysis was performed by using a motion equation. The sizes of the respective portions shown with reference symbols in FIG. 10 are shown in Table 1 below.

TABLE 1

| Movable portion size L1 | 500 μm |
| Movable portion size L2 | 400 μm |
| Movable portion thickness H | 10 μm |
| Support portion length W1 | 40 μm |
| Support portion width W2 | 4 μm |
| Support portion thickness H | 4 μm |
| Material Young's modulus (Si)E | 130.8 GPa |
| Material Poisson ratio (Si)v | 0.28 |
| Resonant frequency f | 6.13 kHz |
| Maximum displacement angle θmax | 12 deg |
| Interelectrode distance d | 42 μm |

The optical scanning element relating to this analytical model caused a pull-in phenomenon at an applied voltage 400V, and the movable portion came into contact with the lower portion. This analytical model assumes a contact type optical scanning element which comes into contact with a lower portion when starting. According to this analytical model, it could be known that the movable portion came into contact with the lower portion when a driving preparation signal (voltage) of 400V or more was applied only when starting, and thereafter, displacement could be repeated by the elastic force of the support portions and a low applied voltage compensating for the shortage.

Next, a production process of the optical scanning element having the same construction as that of the embodiment described above will be described.

Figure 12:
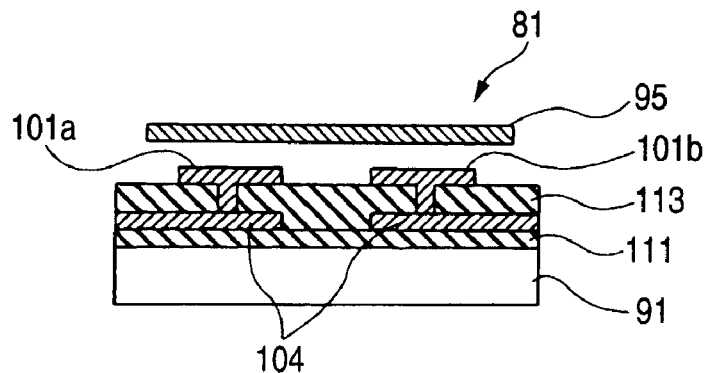
FIG. 12 is a sectional view showing the structure of the optical scanning element used in the production process.

FIG. 12 is a sectional view showing the structure of an optical scanning element used in the production process, and FIGS. 13A-13E are explanatory views showing the production steps of the optical scanning element.

Figure 13A:
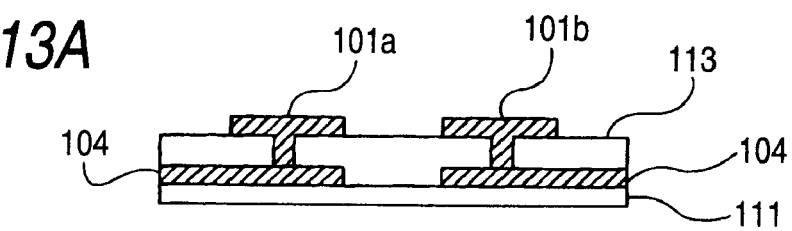
FIGS. 13A-13E are explanatory views showing production steps of the optical scanning element.

To manufacture the optical scanning element 81 shown in FIG. 12 having the same construction as that of the above-described embodiment, first, as shown in FIG. 13A, a drive circuit 104 including a CMOS is formed on a first insulating layer 111 of an SOI (Si on Insulator) substrate 91. At the upper part of the drive circuit 104, $SiO_2$ is deposited by PECVD to form a second insulating layer 113, and contact holes for connecting the output of the drive circuit 104 to the electrodes of the element are pattern-formed by photolithography and fluorine-based RIE etching.

Thereafter, a base layer TiN thin film is deposited by sputtering, and subsequently, W is deposited by sputtering. Accordingly, W is embedded in the contact holes. Further, the surface of W is planarized by CMP, whereby the second insulating layer 113 having contact holes filled with W is formed.

At the upper part of the second insulating layer, Al as fixed electrode films (preferably, an Al alloy containing a high-melting-point metal) is deposited by sputtering, and patterning into a desired electrode shape is performed by photolithography and chloride-based RIE etching to form fixed electrode films (first driver 101a and second driver 101b). At this time, the fixed electrode films are connected to the output of the drive circuit 104 via the contact holes and supplied with potentials.

Figure 13B:
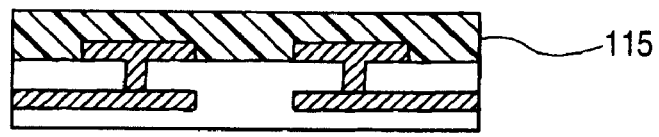

Next, as shown in FIG. 13B, a positive resist film 115 is coated as a sacrifice layer and hard-baked. Hard-baking is performed at a temperature over 200° C. while irradiating Deep UV. Accordingly, the film keeps its shape even in subsequent high-temperature processes, and becomes insoluble into a resist remover solvent. By applying and depositing the resist, the resist surface becomes plane regardless of the level difference of the base film. This resist layer serves as a sacrifice layer, and is removed in a subsequent step. Therefore, the film thickness of the resist after hard-baking determines future gaps between the lower fixed electrodes 101a and 101b and the support portions and the movable portion 95.

Then, portions which become columnar supports for supporting the movable portion are patterned by photolithography and contact holes are formed.

Figure 13C:
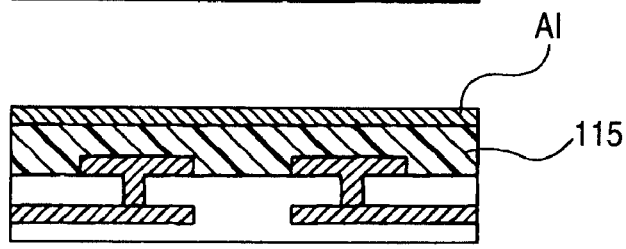

Next, as shown in FIG. 13C, Al which is the movable portion 95, the support portions (elastic support beams 97), and the columnar support of the movable portion 95 (Al alloy preferably containing a high-melting-point metal) is deposited by sputtering.

Figure 13D:
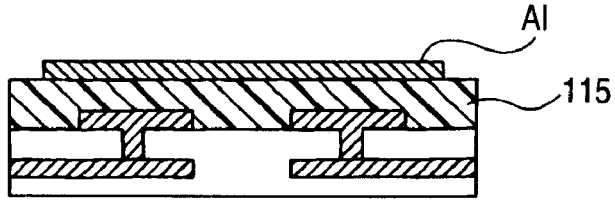

Then, as shown in FIG. 13D, portions which become the movable portion 95, the elastic support beams 97, and columnar supports of the movable portion 95 are pattern-formed by photolithography using a positive resist and fluorine-based RIE etching. Thereafter, the resist is removed by oxygen-based plasma etching (ashing).

Figure 13E:
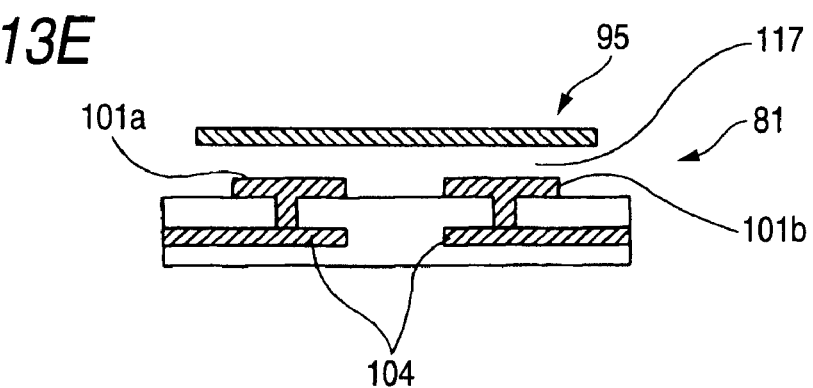

Last, as shown in FIG. 13E, a gap 117 is formed by removing the resist layer 115 as a sacrifice layer by oxygen-based and/or fluorine-based plasma etching (ashing), whereby the optical scanning element 81 having a desired structure is formed.

The materials and production method described above are examples, and any materials and production methods may be used as long as these conform to the spirit of the present invention.

As described above, according to the optical scanning probe 100 of the present embodiment, the optical scanning element 81 which scans light across the subject 53 and the drive voltage control circuit 105 which switches a drive signal for making the optical scanning element 81 scan light are provided, the optical scanning element 81 includes the movable portion 95 having the micro mirror 83 which is displaced in the first rotating direction and the second rotating direction and the first driver 101a and the second driver 101b which apply physical acting forces to the movable portion 95, the drive voltage control circuit 105 has a function for switching a driving preparation signal for attracting the movable portion 95 in either the first rotating direction or the second rotating direction into a scanning drive signal for attracting the movable portion 95 in the first rotating direction and the second rotating direction alternately, and the maximum voltage of the driving preparation signal is set to be a value higher than the maximum voltage of the scanning drive signal, so that by using a high voltage only when starting, the voltage can be lowered when driving. In addition, driving can increase the effect of the elastic force of the elastic support beams 97, so that high-speed driving is possible. As a result, low-voltage high-speed driving is realized by a simple structure.

The optical scanning probe device 31 includes the optical scanning probe 100, the signal processing device 33 which obtains one-dimensional or two-dimensional distribution information of light emitted from an irradiation point in the subject 53 from reflected light guided from the optical fiber 43 of the optical scanning probe 100 and the drive signal of the scanning driver 49, and a display unit 35 which displays video signals output from the signal processing device 33, so that while performing high-speed optical scanning with a low voltage by using the optical scanning probe 100 having a simple structure, the intensity of light emitted from the irradiation point is input as an electric signal into the signal processing device 33, and distribution information of light emitted from this irradiation point can be displayed with high responsiveness at the display unit 35.

According to the control method of the optical scanning probe 100, the scanning drive signal is a drive signal which repeats the process in which elastic energy is stored in the elastic support beams 97 supporting the movable portion 95 until the movable portion 95 is displaced in the one rotating direction, and the movable portion 95 is displaced by a physical acting force generated by the one driver (for example, the first driver 101a), and thereafter the physical acting force from the one driver is made to disappear and the elastic energy stored in the elastic support beams 97 is released, whereby while re-storing elastic energy with polarity reverse to that of the aforementioned elastic energy in the elastic support beams 97, the movable portion 95 is displaced in the other rotating direction, and the movable portion 95 is displaced by a physical acting force generated by the other driver (for example, the second driver 101b). Therefore, before inserting the probe of the optical scanning probe 100 into the subject 53, the movable portion 95 is inclined with a comparatively high voltage driving preparation signal, and from this state, application of the high voltage driving preparation signal is stopped, and the probe is inserted into the subject 53. After insertion into the subject 53, the movable portion 95 is continuously driven with a low voltage. Accordingly, without making the structure and the production process complicated, high-speed scanning and a lower voltage can be realized at the same time while keeping a simple structure by devising the driving method.

Next, other construction examples of the above-described optical scanning element will be described.

<Variation 1>

Figure 14:
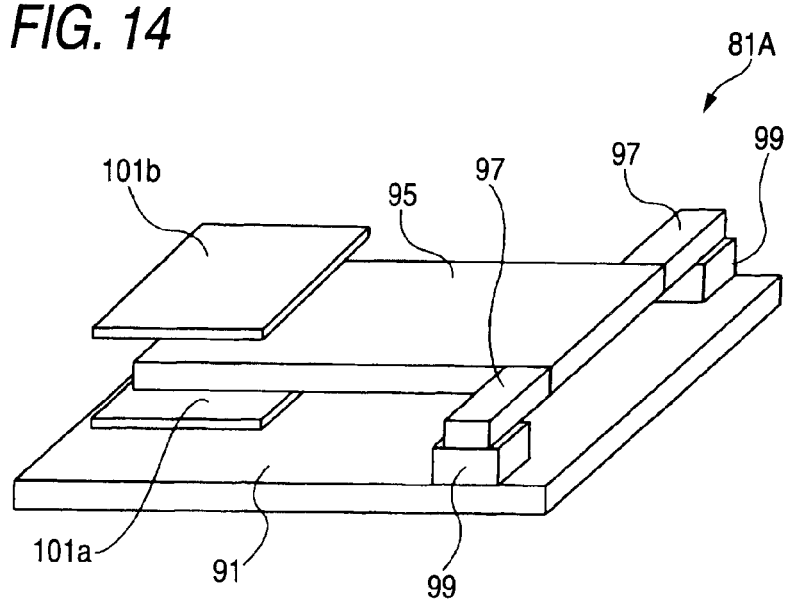
FIG. 14 is a perspective view of the optical scanning element of Variation 1 in which the movable portion is supported by a cantilevered structure.

FIG. 14 is a perspective view of an optical scanning element of Variation 1 in which the movable portion is supported by a cantilevered structure.

The optical scanning element of the present invention can be constructed so that the movable portion 95 is supported by a cantilevered structure. In other words, in the optical scanning element 81A, one end of the movable portion 95 is supported and fixed to the substrate 91 via the elastic support beams 97 and 97 and spacers 99 and 99. In other words, the movable portion 95 is cantilevered so that the other end becomes a free end. Then, on the substrate 91, the first driver 101a is provided so as to face the free end of the movable portion 95, and on the opposite side of the first driver 101a to the movable portion 95, the second driver 101b to be formed on a counter substrate that is not shown is provided.

In the optical scanning element 81A thus constructed, the movable portion 95 is also swung and displaced around the elastic support beams 97 as a twist center by applying a voltage to the first driver 101a, the second driver 101b, and the movable electrode 103. Then, the movable portion 95 is the micro mirror 83, so that the light reflection direction is changed.

<Variation 2>

Figure 15:
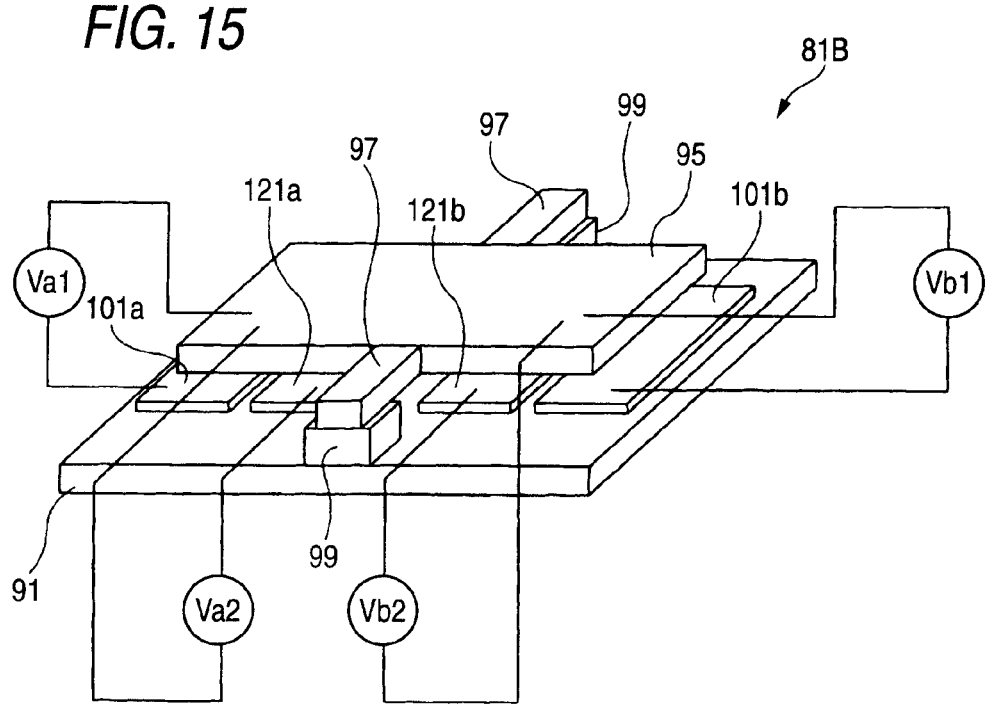
FIG. 15 is a perspective view of the optical scanning element of Variation 2 constructed so that two physical acting forces can be set in the switching direction of the movable portion.
Figure 16A:
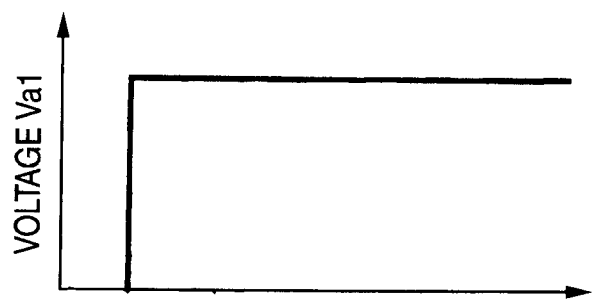
FIG. 16A-16E are correlation diagrams between the rotation angle and applied voltage, showing a driving example of the optical scanning element of Variation 2.
Figure 16B:
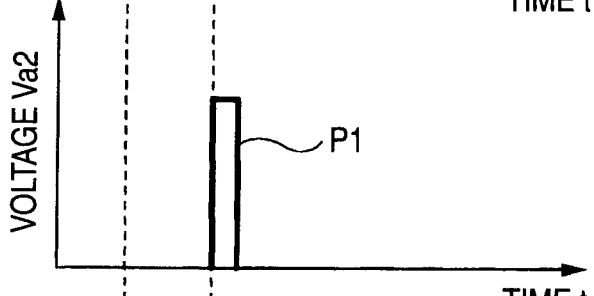
Figure 16C:
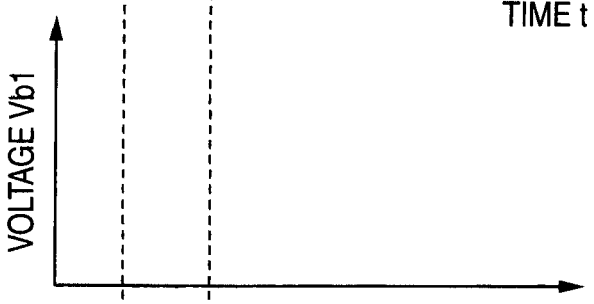
Figure 16D:
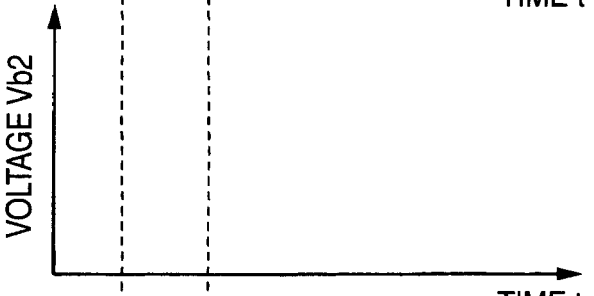
Figure 16E:
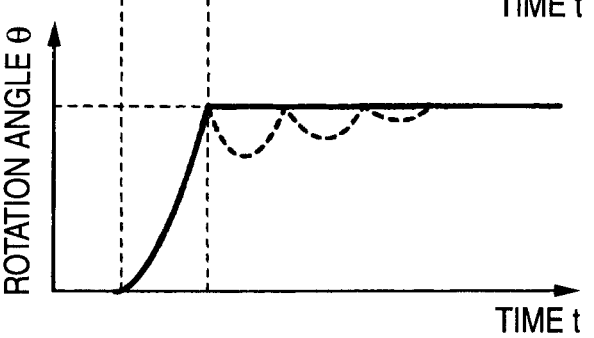

FIG. 15 is a perspective view of the optical scanning element of Variation 2 constructed so that two physical acting forces can be set in the switching direction of the movable portion.

The optical scanning element 81 may be constructed so that two or more physical acting forces can be set in each switching direction of the movable portion. For example, in a swing type movable portion 95 whose center is a rotation center, two or more physical acting forces are applied to each of both sides across the rotation center. Accordingly, different magnitudes of both braking forces can be applied to the one side of the movable portion 95 at different timings, and for example, various braking effects such as braking at a position just before contact of the movable portion 95 by applying an attracting force reverse to the rotating direction can be obtained.

In detail, the optical scanning element 81B includes a first oscillation control electrode 121a and a second oscillation control electrode 121b different from the first driver 101a and the second driver 101b. An oscillation control voltage Va1 is applied between the movable electrode of the movable portion 95 and the first driver 101a, and an oscillation control voltage Va2 is applied between the movable electrode of the movable portion 95 and the second oscillation control electrode 121a. An oscillation control voltage Vb1 is applied between the movable electrode of the movable portion 95 and the second driver 101b, and an oscillation control voltage Vb2 is applied between the movable electrode of the movable portion 95 and the second oscillation control electrode 121b. The first oscillation control electrode 121a and the second oscillation control electrode 121b are disposed outside the first driver 101a and the second driver 101b, respectively, opposite to those in the construction of the present embodiment.

In this optical scanning element 81B, the physical acting forces of the first oscillation control electrode 121a and the second oscillation control electrode 121b which displace the movable portion 95 are electrostatic forces similar to the first driver 101a and the second driver 101b. As an operation example of this optical scanning element 81B, in the case of contact driving, for example, the movable portion 95 is rotatively displaced to the first driver 101a side, and immediately before coming into contact with the pivot that is a stopper member not shown, the oscillation control voltage Vb2 is applied between the movable electrode of the movable portion 95 and the second oscillation control electrode 121b.

When an electrostatic force thus acts in the direction reverse to the displacement direction of the movable portion 95, the movable portion 95 immediately before coming into contact with the stopper member is decelerated, and the movable portion 95 is prevented from reaching the final displaced position at a high speed or displacement in the direction reverse to the displacement direction of the movable portion 95 by a reactive force after coming into contact with the stopper member, and the oscillation of the movable portion 95 is actively reduced. In other words, the electrostatic force generated according to the oscillation control voltage Vb2 acts as a braking force (brake) against the moment of the movable portion 95. Accordingly, the movable portion 95 is controlled so as to stand still while coming into contact with the stopper member.

Accordingly, oscillation according to collision caused when the movable portion 95 reaches the final displaced position at a high speed and overshoot, when reaching the final displaced position in the case of non-contact driving, do not occur.

FIG. 16A-16E are correlation diagrams between the rotation angle and the applied voltage in another driving example of the optical scanning element of Variation 2.

After the optical scanning element 81B drives and displaces the movable portion 95 in the first rotating direction, when the movable portion 95 tries to switch to the second rotating direction, or during switching, pulse P1 is applied to the movable electrode of the movable portion 95 and the first oscillation control electrode 121a, whereby an electrostatic force in the first rotating direction is applied to the movable portion 95. After the movable portion 95 is driven and displaced in the first rotating direction and reaches the final displaced position, further, while the movable portion 95 switches to the second rotating direction according to a reactive force or an elastic force according to contact with the stopper member, an electrostatic force in the first rotating direction is applied to the movable portion 95, whereby the movement (the wave-like locus shown by the dashed line in the drawing) of the movable portion 95 to separate from the final displaced position is actively braked. Accordingly, the movable portion 95 can be quickly made to stand still at the final displaced position.

<Variation 3>

Figure 17:
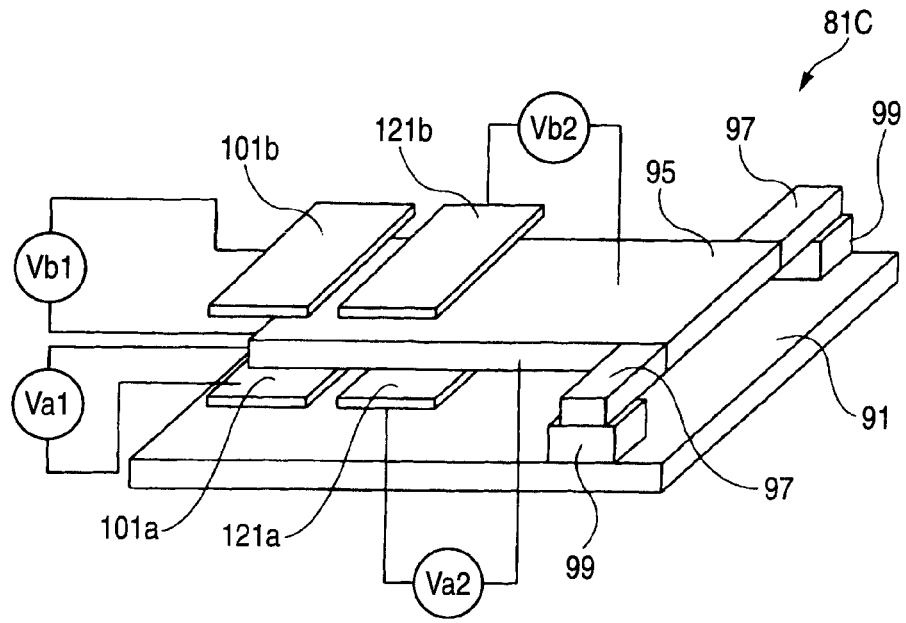
FIG. 17 is a perspective view of the optical scanning element of Variation 3 constructed so that two physical acting forces can be set in the switching direction of the movable portion by a cantilevered structure.

FIG. 17 is a perspective view of an optical scanning element of Variation 3 constructed so that two physical acting forces can be set in the switching direction of the movable portion by a cantilevered structure.

The optical scanning element 81C is constructed so that one end of the movable portion 95 is supported and fixed to the substrate 91 via the elastic support beam 97 and the spacer 99, the first driver 101a and the first oscillation control electrode 121a are provided on the substrate 91 so as to face the free end of the movable portion 95, and the second driver 101b and the second oscillation control electrode 121b formed on a counter substrate not shown are provided on the opposite side of the first driver 101a and the first oscillation control electrode 121a across the movable portion 95.

In the optical scanning element 81C thus constructed, the oscillation control voltage Va2, Vb2 described above is also applied between the first oscillation control voltage 121a and the movable portion 95 or between the second oscillation control electrode 121b and the movable portion 95, and the oscillation of the movable portion 95 can be actively reduced. Accordingly, the displacement operation in the optical scanning element 81C can be increased in speed.

The optical scanning element described above performs a uniaxial swing operation, and in this case, the optical scanning element is applied to, in particular, a laser beam tomographic device (OCT: Optical Coherence Tomography).

Figure 18:
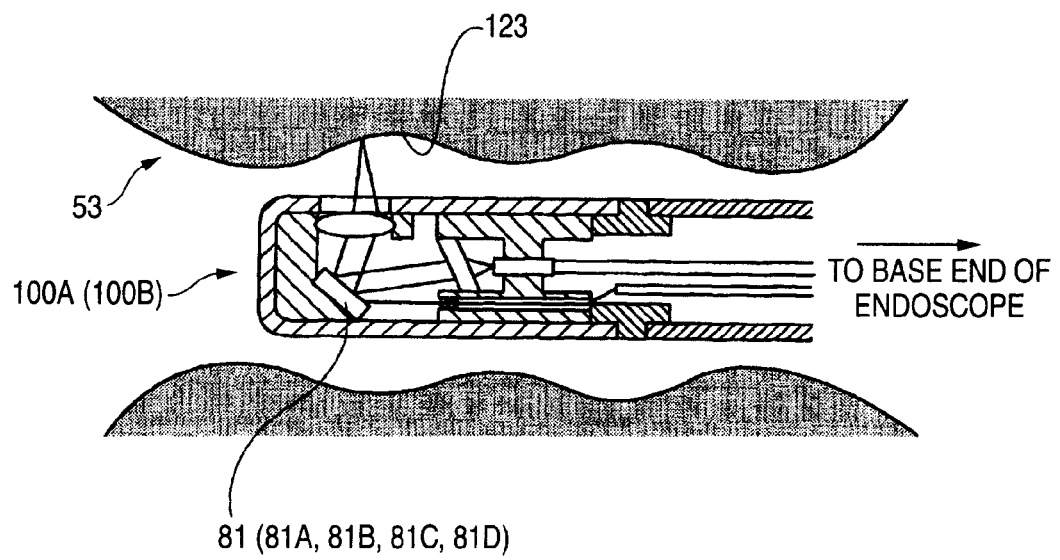
FIG. 18 is an explanatory view showing an observation state of the inside of a living body tissue by using the optical scanning element of the present invention.

FIG. 18 is an explanatory view showing an observation state of the inside of a living body tissue by using the optical scanning element of the present invention.

The optical scanning elements 81, 81A, 81B, and 81C described above which are swung and displaced uniaxially (that is, one-dimensional scanning) by the elastic support beams 97 can be preferably used in the optical scanning probe 100A of an OCT system. The OTC system is a system for observation of the inside of a body cavity devised based on the Michelson interferometer, and by using low-coherent light, the inside of a living body tissue can be observed. By using this OCT system, the condition inside the living body tissue 123 can be observed on the display unit as a high-quality tomographic image. In the optical scanning element 81 of the illustrated example, the rotation axis is arranged perpendicularly to the paper plane.

Next, an optical scanning element which can swing biaxially will be described.

Figure 19:
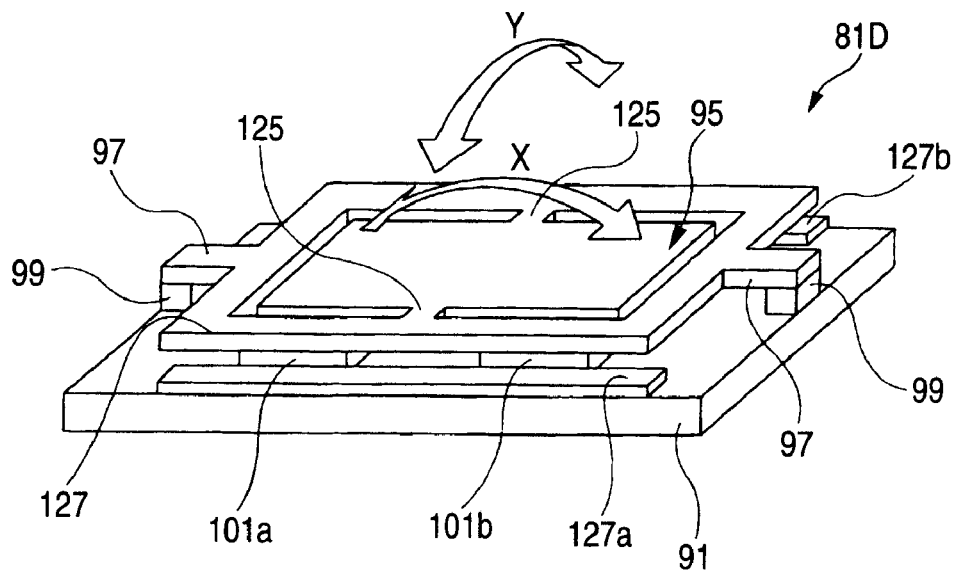
FIG. 19 is a perspective view of a biaxial scanning element.

FIG. 19 is a perspective view of a biaxial scanning element.

In the optical scanning element 81D, the movable portion 95 is supported to be rotatively displaceable in biaxial directions around the elastic support beams 97 as a first rotation axis when the movable portion 95 is displaced in the first and second rotating directions and elastic support beams 125 as a second rotation axis orthogonal to the elastic support beams 97. In this case, the two-dimensional optical scanning element 81D is provided with a third driver 127a and a fourth driver 127b in addition to the first driver 101a and the second driver 101b.

In the optical scanning element 81D, the movable portion 95 is driven in the X direction by voltage application between the first driver 101a or second driver 101b and the movable portion 95, and the movable portion 95 is driven in the Y direction by voltage application between the third driver 127a or fourth driver 127b and the frame 129. In the optical scanning element 81D, the movable portion 95 is two-dimensionally driven to be rotatively displaced around the first rotation axis and the second rotation axis orthogonal to each other, and can perform two-dimensional scanning based on outgoing light and reflected light, and can form an image of an irradiated region based on distribution information of the reflected light.

In this three-dimensional scanning element 81D, after a driving preparation signal is applied and then the probe is inserted into the subject 53, low-voltage high-speed driving is also realized by a simple structure by applying a necessary minimum scanning drive signal.

The optical scanning element in this case is applied to, in particular, a confocal endoscope system.

As shown in FIG. 18, the optical scanning element 81D described above which is swung and displaced biaxially (that is, two-dimensional scanning) by the elastic support beams 97 and the elastic support beams 125 can be preferably used in an optical scanning probe 100B of a confocal endoscope system. The confocal endoscope system has a confocal extractor which extracts only reflected light on a focal plane of an objective optical system by a pinhole (the ferrule 71 serves as the pinhole in the present invention) from reflected light obtained by scanning the surface or a cross section of the living body tissue 123 by a micro mirror. Accordingly, two-dimensional information of the surface of the living body tissue 123 or three-dimensional information (cross section information) including information in the depth direction can be observed as a high-quality image on the display.

Herein, an example in which the optical scanning element is provided with a sealed structure under reduced pressure will be described.

Figure 20:
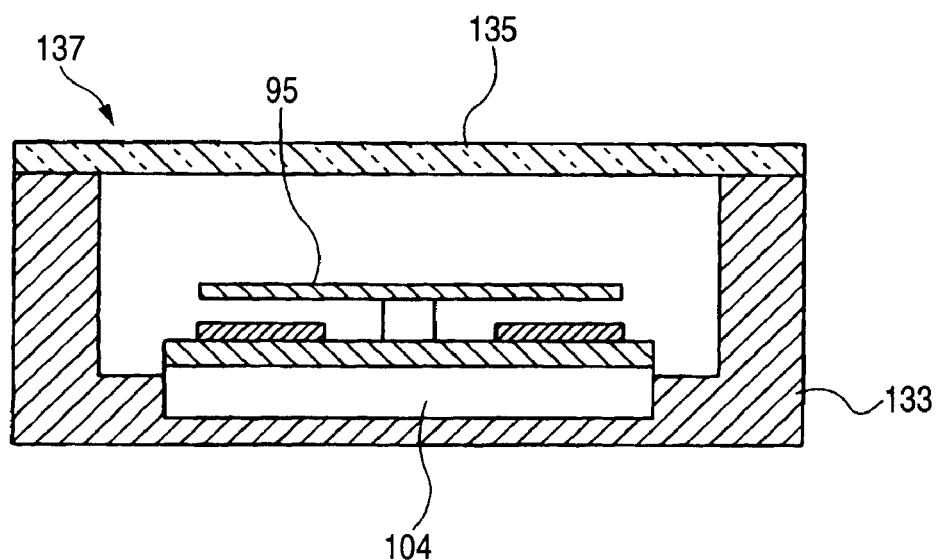
FIG. 20 is a longitudinal sectional view showing a construction example of an optical scanning element sealed under a reduced pressure.

FIG. 20 is a longitudinal sectional view showing a construction example of the optical scanning element which was sealed under reduced pressure.

The optical scanning element 81, etc., described above may have a sealed structure in which at least the movable portion 95 is sealed under reduced pressure. For example, the optical scanning element 81 is housed in a package 133 and the internal space of the package 133 is sealed by a transparent cover glass 135 under reduced pressure lower than the atmospheric pressure. Below the optical scanning element 81 inside the package 133, the drive circuit 104 (see FIG. 5, also) to be electrically connected to the respective electrodes of the optical scanning element 81 is arranged, and have a function for inputting and outputting drive signals after sealing the package 133 of the optical scanning element 81.

According to this package element 137, the movable portion 95 of the optical scanning element is driven under reduced pressure, so that high-speed driving less influenced by the air viscosity is possible. By setting the degree of vacuum herein to, for example, 0.1 atmospheres or less, the influence of the air viscosity can be reduced to a sufficiently low level in practical use. Then, by arranging the package element 137 at the position of the optical scanning element 81 of FIG. 3 described above, an optical scanning probe device which can perform image-taking at a higher speed is obtained.

Figure 21:
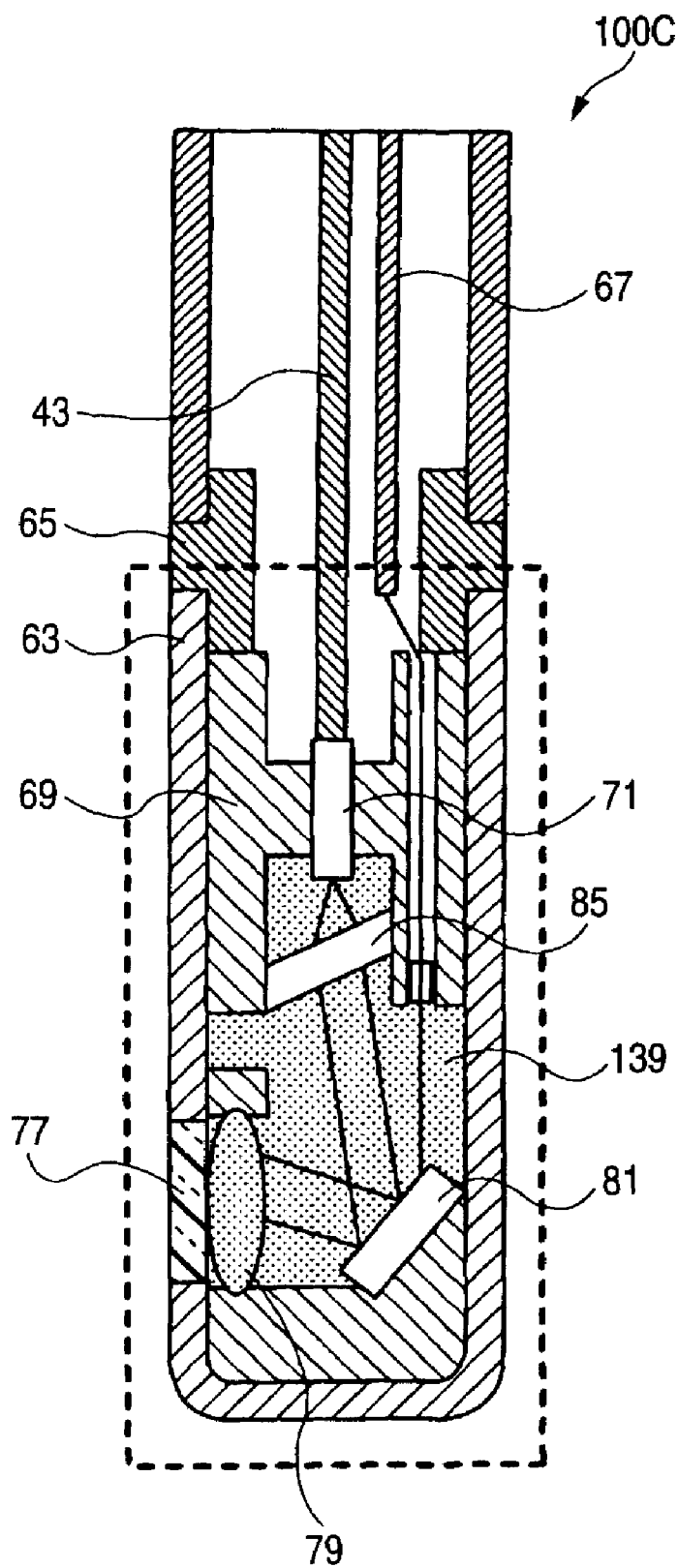
FIG. 21 is an explanatory view showing a case where the internal space of a tip end frame of the optical scanning probe is reduced in pressure.
Figure 22A:
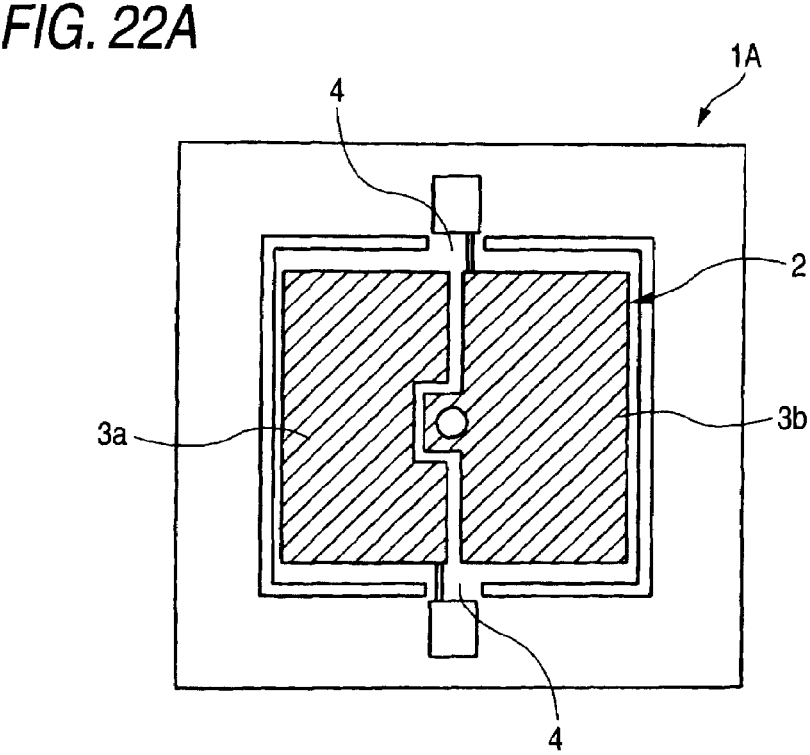
FIGS. 22A and 22B are plan views of a general uniaxial optical scanning element (FIG. 22A), and a biaxial optical scanning element (FIG. 22B)
Figure 22B:
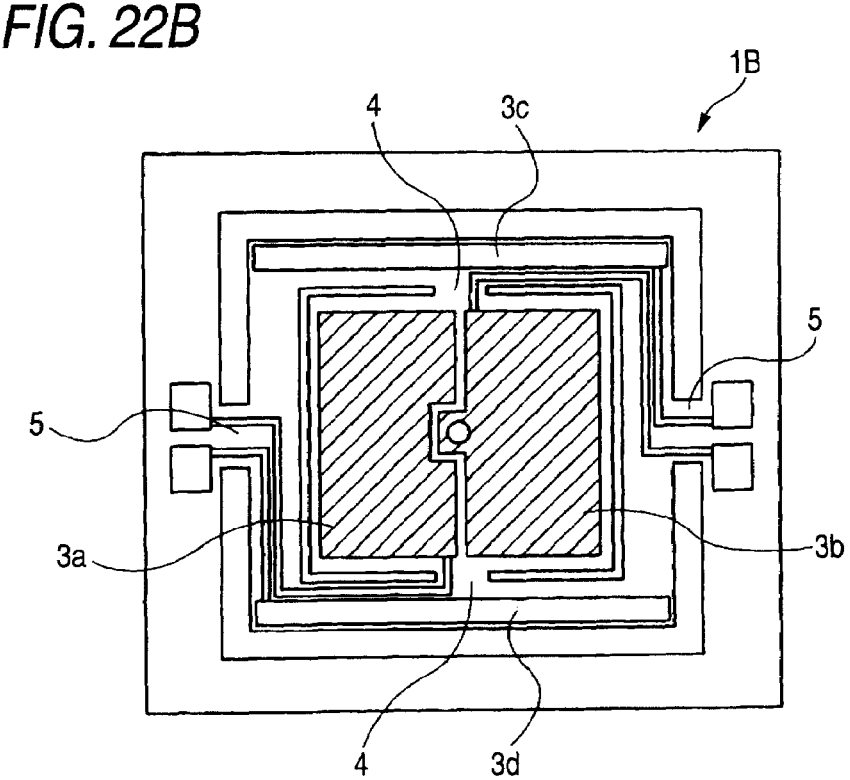
Figure 23:
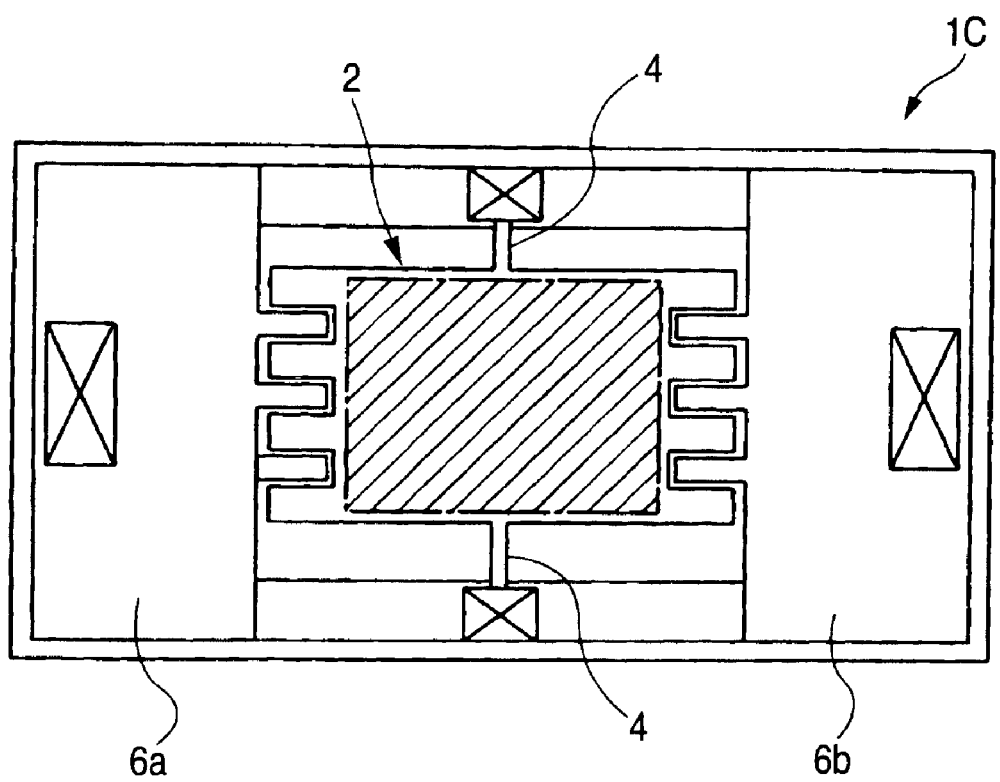
FIG. 23 is a plan view of an optical scanning element having a comb electrode structure.
Figure 24A:
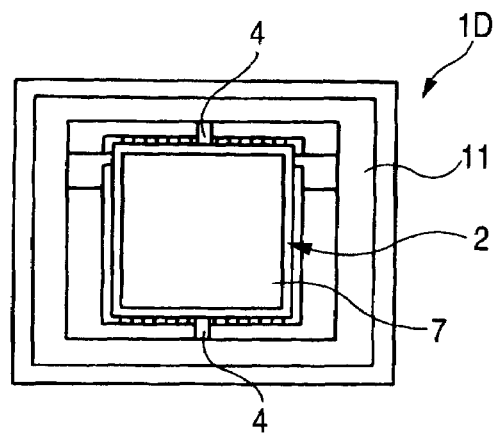
FIGS. 24A-24D are construction views of an optical scanning element in which counter electrodes are provided on inclined surfaces.
Figure 24B:
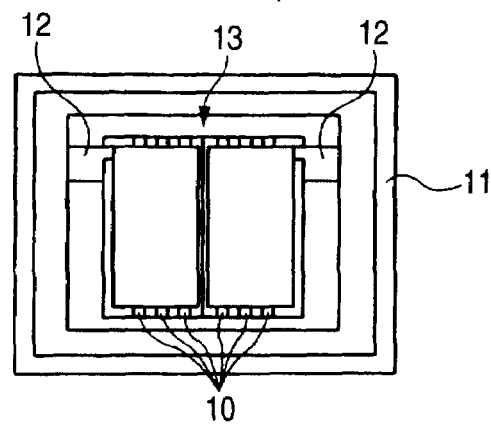
Figure 24C:
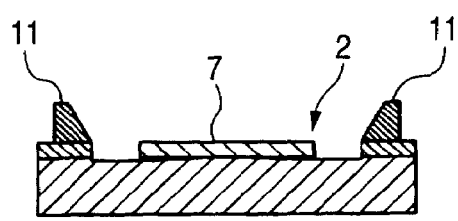
Figure 24D:
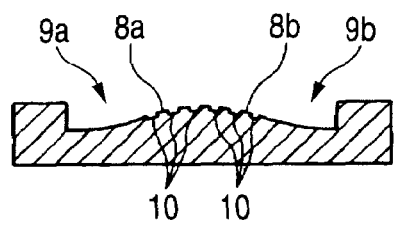
Figure 25A:
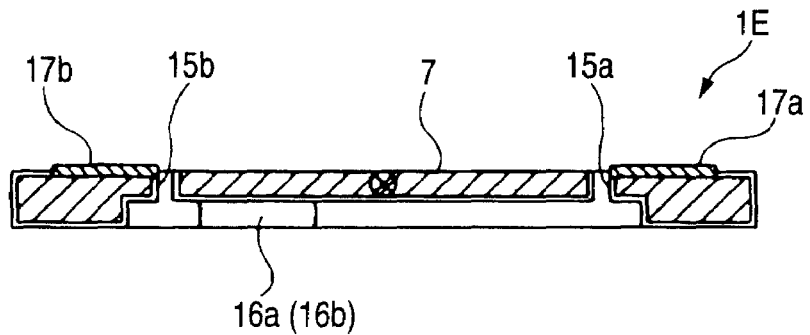
FIGS. 25A and 25B are views showing a conventional optical scanning element including starting fixed electrodes.
Figure 25B:
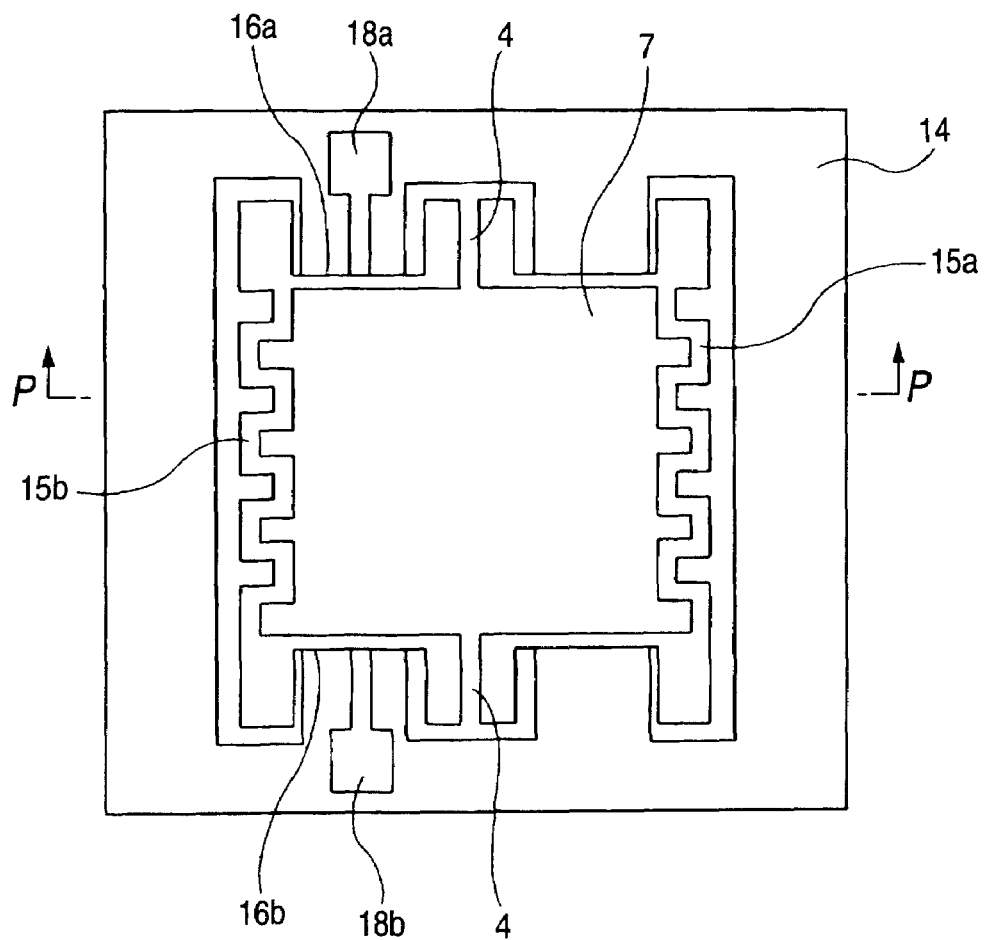
Figure 26:
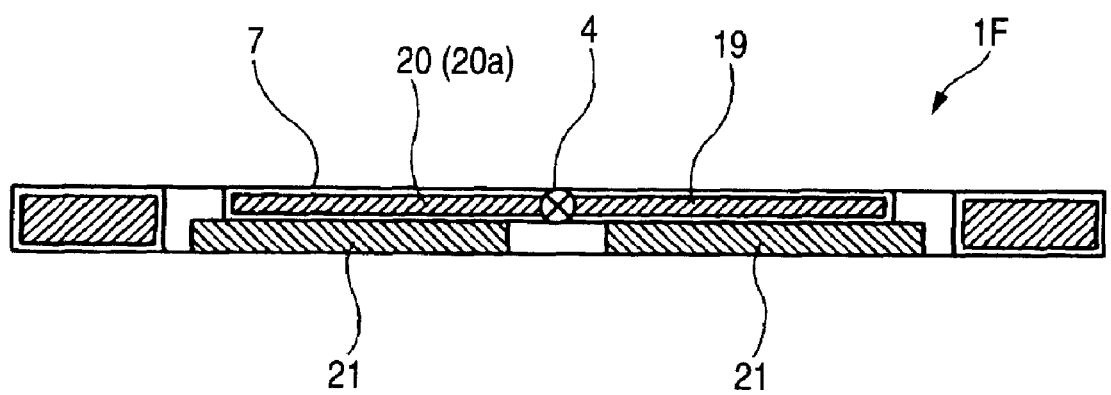
FIG. 26 is a construction view of a conventional optical scanning element including fixed electrodes deviated in the thickness direction of the reflecting means holding substrate, wherein description of some numerals and symbols in the drawings are set forth below.

Other than sealing of the optical scanning element into a package, for example, the structure shown in FIG. 21 is also allowed.

FIG. 21 is an explanatory view showing a case where the internal space of the tip end frame of the optical scanning probe is reduced in pressure.

In the optical scanning probe 100C, by defining a reduced-pressure space 139 to be lower than the atmospheric pressure inside the tip end frame 63, it becomes unnecessary to seal the optical scanning element 81 alone under reduced pressure, so that the structure is simplified. In detail, the members circled by the dotted line in the figure are manufactured under reduced pressure, and after being sealed, they are fixed to the joint 65.

The above-described optical scanning probe is preferably used in confocal optical system optical scanning devices, laser beam tomographic devices (OCT), and blood vessel optical scanning probe devices, etc., and is applicable to medical endoscope devices such as peroral endoscopes, bronchoscopes, and colonoscopies, industrial endoscope devices, and any other endoscope devices.

What is claimed is:

1. An optical scanning probe for observing an inside of a subject by scanning and irradiating a region inside the subject with light and detecting light emitted from an irradiated point of the region, the optical scanning probe comprising:
an optical scanning element that is disposed in a tip end portion of the probe and that optically scans the region inside the subject with light guided to the tip end portion through a light transmitting section inserted in the probe; and
a signal switching section that switches drive signals for making the optical scanning element perform optical scanning, wherein
the optical scanning element includes: a movable portion having a micro mirror that is supported so as to be elastically displaced and that is displaced bidirectionally in a first rotating direction and a second rotating direction that is a reverse direction of the first rotating direction; a first driver that applies a physical acting force in the first rotating direction to the movable portion; and a second driver that applies a physical acting force in the second rotating direction to the movable portion, the signal switching section has a function for switching between a scanning preparation signal and a scanning drive signal and outputting the switched signal, wherein the scanning preparation signal is for attracting the movable portion in one of the first rotating direction and the second rotating direction in response to a timing signal before the probe is inserted into the subject, and the scanning drive signal is for attracting the movable portion alternately in the first rotating direction and the second rotating direction, and a maximum voltage of the scanning preparation signal is set to be higher than a maximum voltage of the scanning drive signal.

2. The optical scanning probe according to claim 1, further comprising a sensor that outputs a detection signal by detecting insertion of the probe into the subject, wherein the detection signal output from the sensor is input as the timing signal into the signal switching section.

3. The optical scanning probe according to claim 1, wherein the timing signal is input into the signal switching section when a power supply to the optical scanning probe is turned on.

4. The optical scanning probe according to claim 1, wherein the timing signal is input by a switch connected to the signal switching section.

5. The optical scanning probe according to claim 1, wherein a final displaced position of the movable portion, when a displacement direction of the movable portion is switched between the first rotating direction and the second rotating direction, is a position at which a lower end of the movable portion comes into contact with a member below the movable portion.

6. The optical scanning probe according to claim 1, wherein a final displaced position of the movable portion, when a displacement direction of the movable portion is switched between the first rotating direction and the second rotating direction, is just before a position at which a lower end of the movable portion comes into contact with a member below the movable portion.

7. The optical scanning probe according to claim 1, wherein the physical acting force is an electrostatic force.

8. The optical scanning probe according to claim 1, wherein the physical acting force is applied to a plurality of points of application of the movable portion.

9. The optical scanning probe according to claim 8, wherein two or more physical acting forces can be set in each of the first and second rotating directions of the movable portion.

10. The optical scanning probe according to claim 1, further comprising a sealing structure that seals at least the movable portion under a reduced pressure lower than an atmospheric pressure.

11. The optical scanning probe according to claim 1, wherein the optical scanning element is supported so that the movable portion can be rotatively displaced biaxially around a first rotation axis for displacement in the first and second rotating directions and a second rotation axis orthogonal to the first rotation axis, and two-dimensionally optically scans the region of the subject.

12. The optical scanning probe according to claim 1, further comprising:

a light source that emits light to be irradiated onto the subject;

a scanning driver that supplies a drive signal for driving and swinging the micro mirror of the optical scanning element; and a return light transmitting section that guides light from the irradiation point of the subject of light two-dimensionally scanned by the optical scanning element to a base end portion.

13. The optical scanning probe according to claim 12, further comprising a pinhole between the light source and the optical scanning element, wherein light passing through the pinhole substantially becomes a point light source to form a confocal optical system between the light source and the subject.

14. The optical scanning probe according to claim 13, wherein the pinhole is formed in a ferruled attached to an end portion of the light transmitting section at the tip end portion of the probe.

15. The optical scanning probe according to claim 1, wherein the light emitted from the irradiation point is one of reflected light, scattered light, fluorescence, and phosphorescence.

16. An optical scanning probe device comprising:
an optical scanning probe according to claim 12;
a signal processor that obtains, from return light guided from the return light transmitting section and a drive signal of the scanning driver, one-dimensional or two-dimensional distribution information of the light emitted from the irradiation point inside the subject; and
a display that displays a video signal output from the signal processor.

17. A method for controlling an optical scanning probe of claim 1, comprising repeating based on the scanning drive signal:

storing a first elastic energy in an elastic support that supports the movable portion, in displacing the movable portion in one direction of the first and second rotating directions;

generating a first physical acting force by one driver of the first and second drivers to displace the movable portion in the one direction;

making the first physical acting force disappear and releasing the first elastic energy stored in the elastic support beam so as to store a second elastic energy having a polarity reverse to that of the first elastic energy in the elastic support beam and to displace the movable portion in the other direction of the first and second rotating directions; and generating a second physical acting force by the other driver of the first and second drivers to displace the movable portion in the other direction.

18. The method for controlling the optical scanning probe according to claim 17, wherein a maximum voltage of the scanning drive signal is set to be less than 100V.

19. The method for controlling the optical scanning probe according to claim 17, wherein the movable portion is displaced with a period corresponding to a resonant frequency of the movable portion.

* * * * *